US006846900B2

(12) United States Patent
Ooga et al.

(10) Patent No.: US 6,846,900 B2
(45) Date of Patent: Jan. 25, 2005

(54) POLYVALENT CARBOXYLIC ACID ESTER, PROCESS FOR PRODUCING THE CARBOXYLIC ACID ESTER, PLASTIC LENS COMPOSITION USING THE CARBOXYLIC ESTER, PLASTIC LENS OBTAINED BY CURING THE COMPOSITION AND PROCESS FOR PRODUCING THE PLASTIC LENS

(75) Inventors: Kazuhiko Ooga, Oita (JP); Tsuneo Tajima, Oita (JP); Kazufumi Kai, Oita (JP); Hiroshi Uchida, Oita (JP)

(73) Assignee: Showa Denko K.K., Tokyo (JP)

( * ) Notice: Subject to any disclaimer, the term of this patent is extended or adjusted under 35 U.S.C. 154(b) by 145 days.

(21) Appl. No.: 10/089,240

(22) PCT Filed: Mar. 7, 2002

(86) PCT No.: PCT/JP02/02155

§ 371 (c)(1),
(2), (4) Date: Mar. 28, 2002

(87) PCT Pub. No.: WO02/079140

PCT Pub. Date: Oct. 10, 2002

(65) Prior Publication Data

US 2003/0144447 A1 Jul. 31, 2003

Related U.S. Application Data

(60) Provisional application No. 60/279,452, filed on Mar. 29, 2001.

(30) Foreign Application Priority Data

Mar. 26, 2001 (JP) ........................................ 2001-086538
Apr. 23, 2001 (JP) ........................................ 2001-124038
Sep. 4, 2001 (JP) ........................................ 2001-266914

(51) Int. Cl.$^7$ ............................................... C08G 63/00

(52) U.S. Cl. ..................... 528/176; 526/318.2; 526/321; 526/329.5; 623/6.11

(58) Field of Search ................................. 528/176, 285; 526/318.2, 321, 329.5, 261; 623/6.11; 524/284; 560/217

(56) References Cited

U.S. PATENT DOCUMENTS

| 4,701,516 A | * | 10/1987 | Rosenquist ................. 528/176 |
| 5,218,067 A | * | 6/1993 | Uchida et al. ............... 526/261 |
| 5,498,751 A | * | 3/1996 | Trapasso et al. ............. 560/217 |
| 6,545,120 B1 | * | 4/2003 | Ooga et al. .................. 528/275 |
| 6,586,508 B1 | * | 7/2003 | Ooga et al. .................. 524/284 |

FOREIGN PATENT DOCUMENTS

| EP | 0 637 597 A1 | 2/1995 |
| WO | WO 99/17137 A1 | 4/1999 |

OTHER PUBLICATIONS

Database Crossfire Beilstein, Beilstein Institut zur Förderung der Chemischen Wissenschaften, Database accession No. 8230765 XP002203080, Abstract.

* cited by examiner

Primary Examiner—Tatyana Zalukaeva
(74) Attorney, Agent, or Firm—Sughrue Mion, PLLC

(57) ABSTRACT

A compound favored with low viscosity, capable of providing a cured product having high refractive index, and suitable for application to optical materials, including plastic lens material, radical polymerizable flame retardant and the like, as well as a process for producing the compound, a plastic lens composition using the compound, a plastic lens obtained by curing the composition and a process for producing the plastic lens. A novel aromatic ring-containing polyvalent (meth)allyl ester derived from a polyvalent carboxylic acid of trivalent or greater valent is employed.

7 Claims, 6 Drawing Sheets

POLYVALENT CARBOXYLIC ACID ESTER, PROCESS FOR PRODUCING THE CARBOXYLIC ACID ESTER, PLASTIC LENS COMPOSITION USING THE CARBOXYLIC ESTER, PLASTIC LENS OBTAINED BY CURING THE COMPOSITION AND PROCESS FOR PRODUCING THE PLASTIC LENS

CROSS-REFERENCE TO RELATED APPLICATION

This application is an application filed under 35 U.S.C. §111(a) claiming benefit, pursuant to 35 U.S.C. §119(e)(1) of the filing date of the Provisional Application 60/279,452 filed Mar. 29, 2001, pursuant to 35 U.S.C. §111(b).

TECHNICAL FIELD

The present invention relates to a novel polyvalent carboxylic acid ester, a process for producing the carboxylic acid ester, a plastic lens composition using the carboxylic acid ester, a plastic lens obtained by curing the composition, and a process for producing the plastic lens.

The novel polyvalent carboxylic acid of the present invention is free of atoms such as halogen atoms or sulfur atoms and can be used as an essential component of a plastic lens composition capable of exhibiting a high refractive index.

The term "plastic lens composition" as used in the present specification refers to a composition used for plastic lenses and the composition may be composed of one kind of a compound or two or more kinds of compounds.

BACKGROUND ART

Polyethylene glycol bis(allyl carbonate) resins represented by CR-39 (trade name, produced by PPG) or diallyl phthalate-based compounds are advantageous in that since the polymerization reaction proceeds at a low speed as compared with acrylic resins, the polymerization reaction is easy to control and a uniform polymerization reaction can be attained. As a result, plastic lenses derived from polydiethylene glycol bis(allyl carbonate) esin or from diallyl phthalate-based compound are educed in the optical strain.

As for polyvalent (meth)allyl esters derived from trivalent or greater polyvalent carboxylic acids, triallyl 1,2,4-benzenetricarboxylate (e.g., TRIAM-705, trade name, produced by Wako Pure Chemical Industries, Ltd.) is known.

However, the refractive index of the cured product of triallyl 1,2,4-benzenetricarboxylate is 1.57 or less and this is excessively low for the refractive index of high refraction lens materials. Furthermore, the cured product is low in impact resistance, and therefore this ester cannot be used as a main component of high refraction plastic lens materials.

As means for dealing with this problem, allyl esters having an allyl ester group at the terminal and internally having the following structure which is derived from a polyvalent saturated carboxylic acid and a polyvalent saturated alcohol, are also known:

wherein R represents a divalent organic residue having from 1 to 20 carbon atoms, B' represents a divalent organic residue derived from a diol, and n is a number from 1 to 20.

These allyl esters provide a cured material having excellent impact resistance. However, since an aliphatic hydrocarbon B' is used inside, even if a terephthalic acid or an isophthalic acid is used as the polyvalent saturated carboxylic acid, the refractive index becomes lower than that of the cured material of diallyl terephthalate monomer or diallyl isophthalate monomer itself. As such, the refractive index is not necessarily satisfactory in use for high refractive index lenses.

Also, a plastic lens composition containing an organic residue derived from a compound having an aromatic ring and two or more hydroxyl groups is proposed in Japanese Unexamined Patent Publication No. 7-138334 (JP-A-7-138334).

In the composition of JP-A-7-138334, the low viscosity cannot be attained unless the amount of the compound having an aromatic ring and two or more hydroxyl groups used is greatly reduced or the reactive monomer is used in a large amount. However, if the amount of the compound having an aromatic ring and two or more hydroxyl groups used is drastically reduced, a high refractive index of 1.58 or more cannot be obtained. Furthermore, if the reactive monofunctional monomer is used in a large amount, the heat resistance disadvantageously deteriorates. Under these circumstances, an ester usable as a main component of lens materials having high refractive index, low viscosity and low specific gravity is in demand.

DISCLOSURE OF INVENTION

In order to solve the above-described problems, the object of the present invention is to provide a compound favored with low viscosity, capable of providing a cured product having high refractive index, and suitable for application to optical materials including plastic lens material, radical polymerizable flame retardant and the like, as well as a process for producing the compound, a plastic lens composition using the compound, a plastic lens obtained by curing the composition and a process for producing the plastic lens.

As a result of extensive investigations to solve the above-described problems, the present inventors have found that a cured product having low viscosity and high refractive index can be obtained using an aromatic ring-containing polyvalent (meth)allyl ester derived from a trivalent or greater valent carboxylic acid. The present invention has been accomplished based on this finding.

The term "(meth)allyl ester" as used herein means an allyl ester and/or a methallyl ester and the term "(meth)allyl alcohol" means an allyl alcohol and/or a methallyl alcohol.

The present invention (I) provides a polyvalent carboxylic acid ester which is a trivalent or greater valent carboxylic acid ester and which has, within one molecule, two or more organic groups represented by the following formula (1) and an organic group represented by the following formula (2):

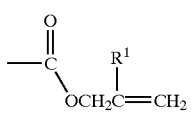

(1)

wherein each $R^2$ independently represents H or $CH_3$;

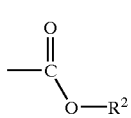

(2)

wherein $R^2$ represents an organic group derived from a compound having an aromatic ring and a hydroxyl group within one molecule.

The present invention (II) provides a process for producing the polyvalent carboxylic acid ester of the present invention (I), comprising at least one of the following Steps (A) and (B):

Step (A)

a step of performing a transesterification reaction between at least one polyvalent (meth)allyl ester derived from a trivalent or greater valent carboxylic acid and one or more hydroxyl group-containing compounds containing, as an essential component, a compound having an aromatic ring and a hydroxyl group within one molecule, in the presence of a catalyst to obtain the polyvalent carboxylic acid ester of the present invention (I);

Step (B)

a step of performing a esterification reaction between at least one member selected from the group consisting of trivalent or greater valent carboxylic acids and anhydrides thereof, and a hydroxyl group-containing compound containing, as essential components, an allyl alcohol and/or a methallyl alcohol and a compound having an aromatic ring and a hydroxyl group within one molecule, in the presence of a catalyst to obtain the polyvalent carboxylic acid ester of the present invention (I).

The present invention (III) provides a plastic lens composition comprising, as an essential component, at least one polyvalent carboxylic acid ester of the present invention (I).

The present invention (IV) provides a plastic lens composition of the present invention (III), further comprising from 0.1 to 10 parts by mass of at least one radical polymerization initiator per 100 parts by mass of whole curable components in the plastic lens composition.

The present invention (V) provides a plastic lens obtained by curing the plastic lens composition of the present invention (III) or (IV).

The present invention (VI) provides a process for producing the plastic lens of the present invention (V), comprising curing the plastic lens composition of the present invention (III) or (IV).

The term "whole curable components" as used in the present specification refers to the total amount of compounds having radical polymerizability contained in the plastic lens composition of the present invention.

BEST MODE FOR CARRYING OUT THE INVENTION

Figure 1:
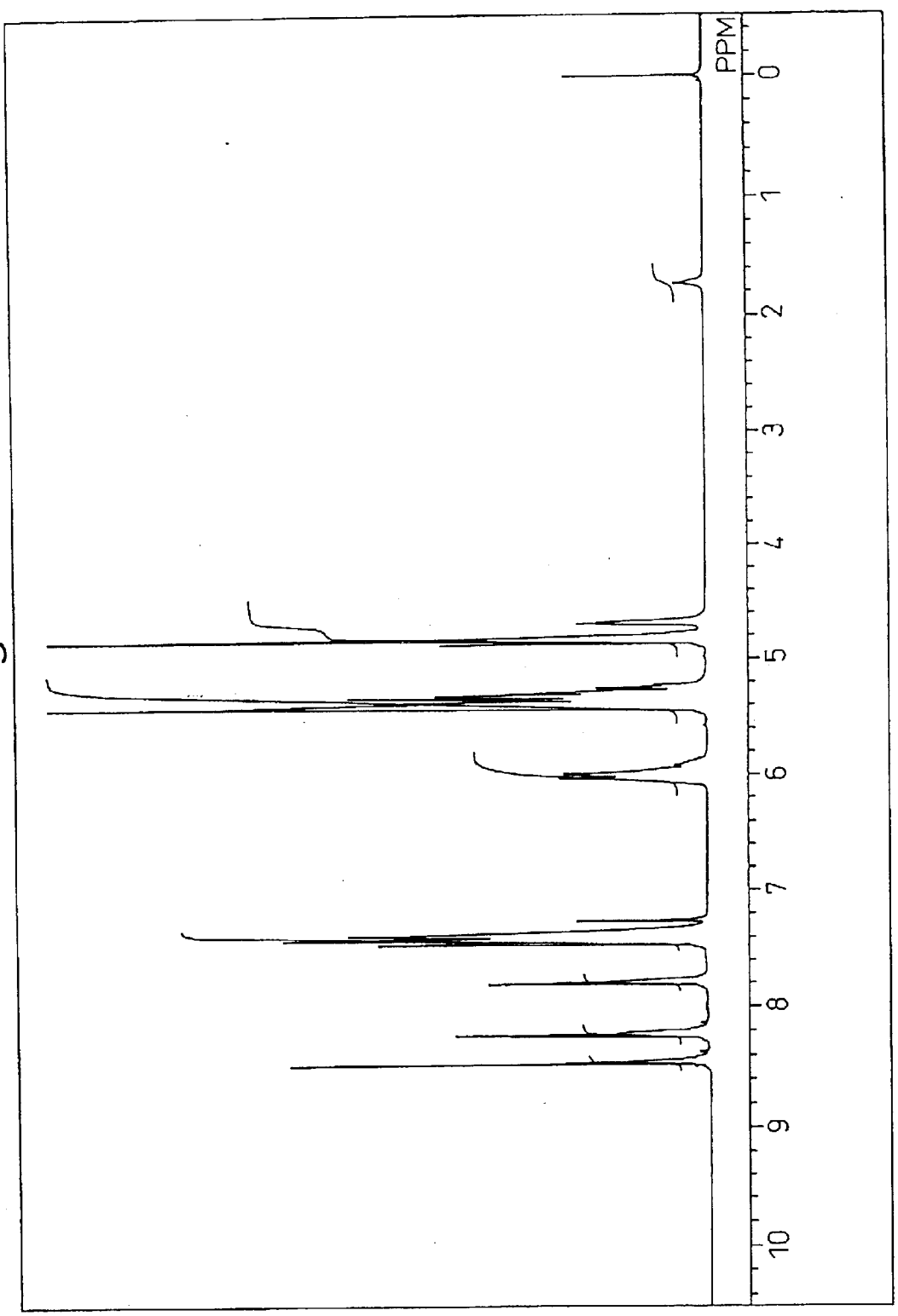
FIG. 1 is a 400 MHz $^1$H-NMR spectrum chart of the allyl ester compound produced in Production Example 1.

The present invention is described in detail below.

The present invention (I) will now be described. The present invention (I) is a polyvalent carboxylic acid ester which is a trivalent or greater polyvalent carboxylic acid ester and which has, within one molecule, two or more organic groups represented by formula (1) above and an organic group represented by formula (2) above:

Examples of the "trivalent or greater valent carboxylic acid" as used include benzenetricarboxylic acid, benzenetetracarboxylic acid, a tricarboxylic acid of alkane having from 3 to 6 carbon atoms, tetracarboxylic acid having from 4 to 6 carbon atoms and an oligomer of acrylic acid. Of course, the present invention is not limited to these examples.

More specific examples of preferred trivalent or greater valent carboxylic acids include 1,3,5-benzenetricarboxylic acid, 1,2,4-benzenetricaboxylic acid, 1,2,3-propanetricarboxylic acid, 1,4,5-benzenetetracarboxylic acid and 1,2,3,4-butanetetracarboxylic acid. Among these, in view of easily availability of starting materials, 1,3,5-benzenetricarboxylic acid, 1,2,4-benznetricarboxylic acid, 1,2,4,5-benzenetetracarboxylic acid and 1,2,3,4-butanetetracarboxylic acid are more preferred, and 1,3,5-benznetricarboxylic acid and 1,2,4-benzenetricarboxylic acid are most preferred.

In formula (1), each $R^1$ independently represents H or $CH_3$.

More specifically, when $R^1$ is H, the compound of formula (1) is an allyl ester and when $R^2$ is $CH_3$, the compound of formula (1) is a methallyl ester.

The term "each $R^1$ independently represents H or $CH_3$" as used herein means that the moieties represented by $R^1$ in the terminal group represented by formula (1) within one molecule of the polyvalent carboxylic acid ester of the present invention (I) may all be H or $CH_3$ or may be partially H with other moieties being $CH_3$.

Taking into account the radical polymerizability of the polyvalent carboxylic acid ester of the present invention (I), the polyvalent carboxylic acid ester of the present invention preferably has at least one allyl group within one molecule, more preferably two or more allyl groups within one molecule.

In formula (2), $R^2$ represents an organic group derived from a compound having an aromatic ring and a hydroxyl group within one molecule.

Preferred examples of the "compound having an aromatic ring and a hydroxyl group within one molecule" include benzyl alcohol, phenol, phenoxyethanol, 2 mol ethylene oxide adduct of phenol, 3 mol ethylene oxide adduct of phenol, 2,4,6-tribromophenol, 2,4,6-tribromophenoxyethanol, 2 mol ethylene oxide adduct of 2,4,6-tribromophenol, 3 mol ethylene oxide adduct of 2,4,6-tribromophenol, methyl p-hydroxyethoxybenzoate, methyl m-hydroxyethoxybenzoate, methyl o-hydroxyethoxybenzoate, phenyl p-hydroxyethoxybenzoate, phenyl m-hydroxyethoxybenzoate, phenyl o-hydroxyethoxybenzoate, benzyl p-hydroxyethoxybenzoate, benzyl m-hydroxyethoxybenzoate and benzyl o-hydroxyethoxybenzoate. Needless to say, the present invention is not limited to these specific examples.

The present invention (II) will now be described. The present invention (II) relates to a process for producing the polyvalent carboxylic acid ester of the present invention (I), comprising at least one of the above-mentioned Steps (A) and (B).

The polyvalent carboxylic acid ester of the present invention (I) can be produced as follows using, for example, the process of Step (A).

Using at least one polyvalent (meth)allyl ester derived from a trivalent or greater valent carboxylic acid in a fixed ratio, esterification with one or more hydroxyl group-containing compounds containing, as an essential component, a compound having an aromatic ring and a hydroxyl group within one molecule is performed in the presence of a catalyst and through this step, the objective compound can be obtained. Of course, the present invention is not limited thereto and a step such as purification may be provided, if desired.

The catalyst for use in Step (A) is not particularly limited insofar as it is a catalyst which can be used for transesterification in general. An organic metal compound is particularly preferred and specific examples thereof include tetraisopropyl titanate, tetra-n-butyl titanate, dibutyltin oxide, dioctyltin oxide, hafnium acetylacetonate and zirconium acetylacetonate. However, the present invention is not limited thereto. Among these, dibutyltin oxide and dioctyltin oxide are preferred.

The reaction temperature in Step (A) is not particularly limited but is preferably from 100 to 230° C., more preferably 120 to 220° C. In the case where a solvent is used, the reaction temperature is sometimes limited by the boiling point of the solvent.

In Step (A), a solvent is usually not used. However, a solvent may be used, if desired. The solvent which can be used is not particularly limited insofar as it does not inhibit the transesterification. Specific examples thereof include benzene, toluene, xylene and cyclohexane. However, the present invention is not limited thereto. Among these, benzene and toluene are preferred. Here, as described above, the step may be performed without using a solvent.

The polyvalent carboxylic acid ester of the present invention (I) can be produced as follows using, for example, the process of Step (B).

Using at least one trivalent or greater valent carboxylic acid in a fixed ratio, esterification with a hydroxyl group-containing compound containing, as essential components, an allyl alcohol and/or a methallyl alcohol and a compound having an aromatic ring and a hydroxyl group within one molecule is performed in the presence of a catalyst and through this step, the objective compound can be obtained. Of course, the present invention is not limited thereto and a step such as purification may be provided, if desired.

The catalyst for use in Step (B) is not particularly limited insofar as it is a catalyst which can be used for esterification in general. However, p-toluenesulfonic acid, methanesulfonic acid, sulfuric acid and hydrochloric acid are preferably used. Among these, p-toluenesulfonic acid, methanesulfonic acid and sulfuric acid are preferred.

The reaction temperature in Step (B) is not particularly limited. However, in Step (B), a solvent is generally used as an entrainer and when a solvent is used in Step (B), the upper limit of the reaction temperature is limited by the boiling point of the solvent.

The solvent which can be used is not particularly limited insofar as it does not inhibit the esterification. Specific examples thereof include benzene, toluene, xylene and cyclohexane. However, the present invention is not limited thereto. Among these, benzene and toluene are preferred.

The plastic lens composition of the present invention (III) and the present invention (IV) is described below.

The present invention (III) is a plastic lens composition comprising at least one polyvalent carboxylic acid ester of the present invention as an essential component.

The present invention (IV) is a plastic lens composition of the present invention (III), further comprising from 0.1 to 10 parts by mass of at least one radical polymerization initiator per 100 parts by mass of whole curable components in the plastic lens composition.

The amount blended of the compound of the present invention (I) based on whole curable components contained in the plastic lens composition of the present invention (III) is not particularly limited. However, for producing a high refractive index lens, the amount blended is preferably 20% by mass or more, more preferably 25% by mass or more, still more preferably 30% by mass or more, though this may vary depending on the kind of other components blended. If the blended amount of the compound is less than 20% by mass, the cured product may fail to have a high refractive index, depending on the kind of other components blended and this is not preferred in the case of obtaining a high refractive index lens.

In the plastic lens composition of the present invention, a polyfunctional compound copolymerizable with the compound of the present invention (I) may be used mainly for the purpose of adjusting the viscosity of the composition and maintaining the heat resistance.

The term "polyfunctional compound" as used in the present specification means a compound having two or more radical polymerizable functional groups within one molecule.

Specific examples of the polyfunctional compound copolymerizable with the compound of the present invention (I) include diallyl biphenyl-2,2'-dicarboxylate, dimethallyl biphenyl-2,2'-dicarboxylate, allylmethallyl biphenyl-2,2'-dicarboxylate, diallyl biphenyl-3,3'-dicarboxylate, dimethallyl biphenyl-3,3'-dicarboxylate, allylmethallyl biphenyl-3,3'-dicarboxylate, diallyl isophthalate, dimethallyl isophthalate, allylmethallyl isophthalate, diallyl phthalate, dimethallyl phthalate, allylmethallyl phthalate, diallyl terephthalate, dimethallyl terephthalate, allylmethallyl terephthalate, triallyl 1,2,4-benzenetricarboxylate, trimethallyl 1,2,4-benzenetricarboxylate, diallylmethallyl 1,2,4-benzenetricarboxylate, allyldimethallyl 1,2,4-benzenetricarboxylte, triallyl 1,3,5-benzenetricarboxylate, trimethallyl 1,3,5-benzenetricarboxylate, diallylmethallyl 1,3,5-benzenetricarboxylate and allyldimethallyl 1,3,5-benzenetricarboxylate.

The amount blended of the polyfunctional compound (hereinafter referred to as "Component (B)") copolymerizable with the compound of the present invention (I) based on whole curable components in the plastic lens composition of the present invention (III) varies depending on the kind of the compound used, but is preferably 80% by mass or less, more preferably 75% by mass or less, still more preferably 70% by mass or less, based on whole curable components. If the amount of Component (B) blended exceeds 80% by mass based on whole curable components, the physical properties of the cured product obtained by curing the plastic lens composition are seriously affected by Component (B) as a blend and the effect of the polyvalent carboxylic acid ester of the present invention (I) cannot be realized with ease.

In the plastic lens composition of the present invention (III), one or more monofunctional compounds (hereinafter referred to as "Component (C)") copolymerizable with the compound of the present invention (I) or Component (B) may be, and is preferably, added mainly for the purpose of adjusting the viscosity of the composition and maintaining the impact strength.

The term "monofunctional compound" as used in the present specification means a compound having one radical polymerizable functional group within one molecule.

Examples of Component (C) include monomers having an acryl group, a methacryl group, a vinyl group, an allyl group or a methallyl group. Specific examples thereof include allyl p-phenylbenzoate, methallyl p-phenylbenzoate, allyl m-phenylbenzoate, methallyl m-phenylbenzoate, allyl o-phenylbenzoate, methallyl o-phenylbenzoate, acryloyloxyethyl-p-phenylbenzoate, methacryloyloxyethyl-p-phenyl benzoate, acryloyloxyethyl-m-phenyl benzoate, methacryloyloxyethyl-m-phenyl benzoate, acryloyloxyethyl-o-phenyl benzoate, methacryloyloxyethyl-o-phenyl benzoate, diphenyl maleate, dibenzyl maleate, diphenyl fumarate, dibenzyl fumarate, vinyl benzoate, allyl α-naphthoate, methallyl α-naphthoate, allyl β-naphthoate, methallyl β-naphthoate, acryloyloxyethyl-α-naphthalene carboxylate, methacryloyloxyethyl-α-naphthalene carboxylate, acryloyloxyethyl-β-naphthalene carboxylate and methacryloyloxyethyl-β-naphthalene carboxylate. Other examples include the compounds represented by the following structural formulae (3) to (32).

(3)
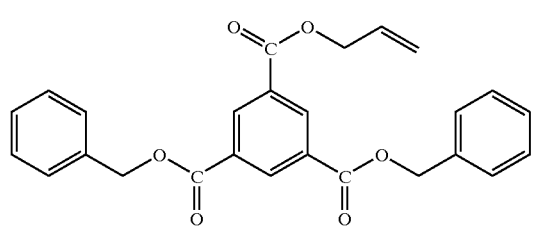

(4)
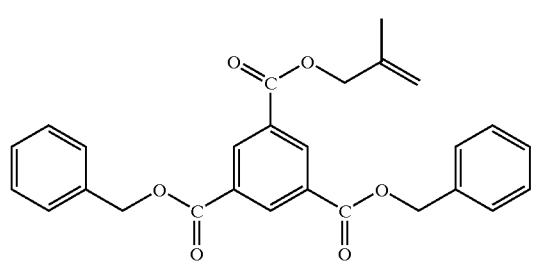

(5)
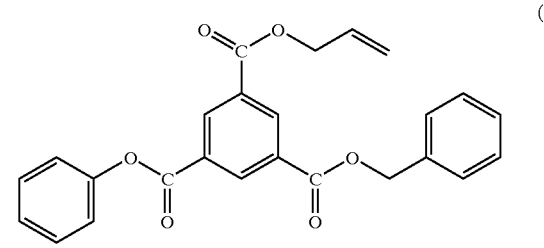

(6)
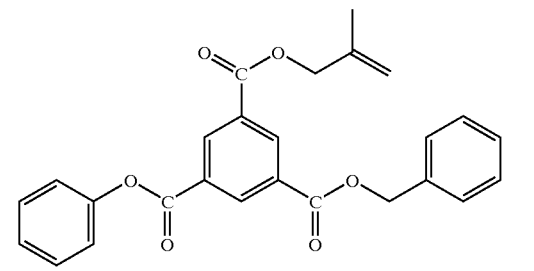

(7)
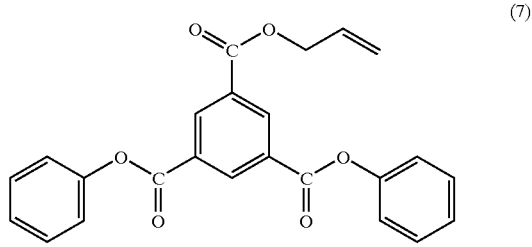

(8)
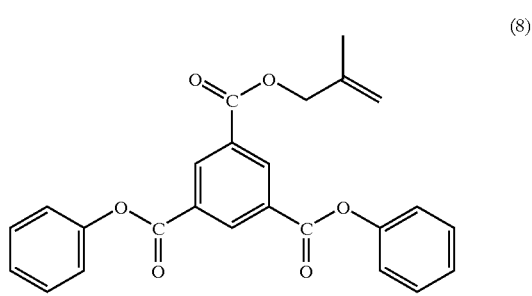

(9)
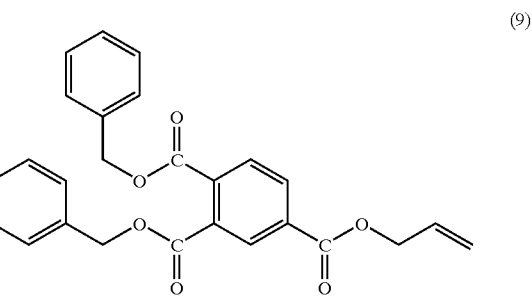

(10)
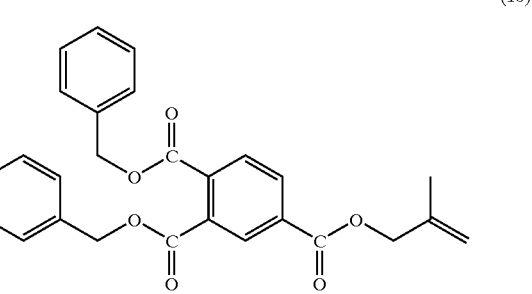

(11)
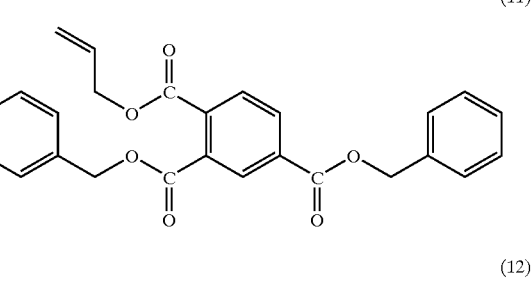

(12)
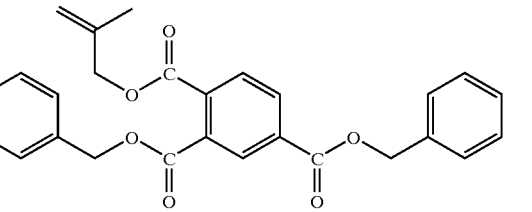

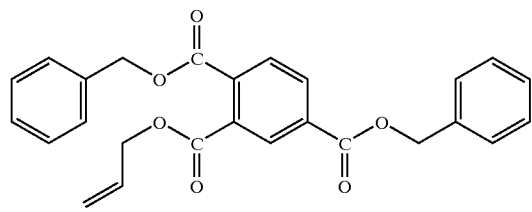
(13)
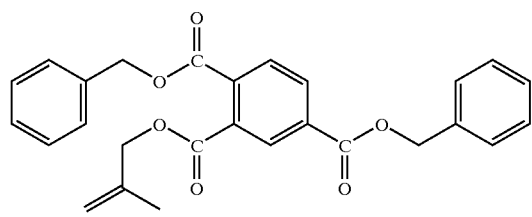
(14)
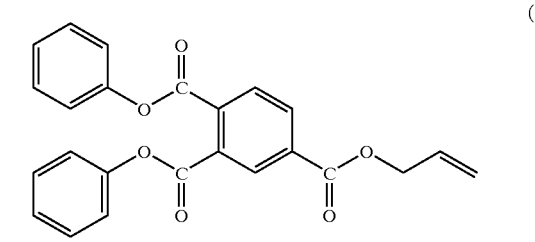
(15)
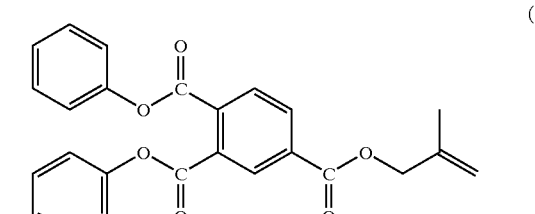
(16)
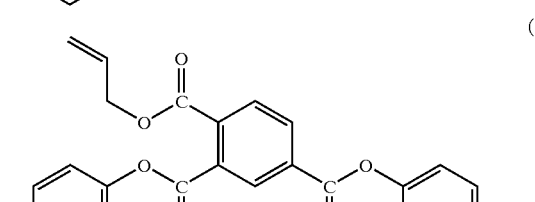
(17)
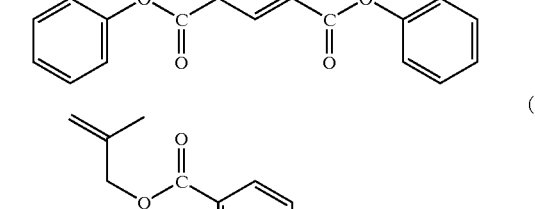
(18)
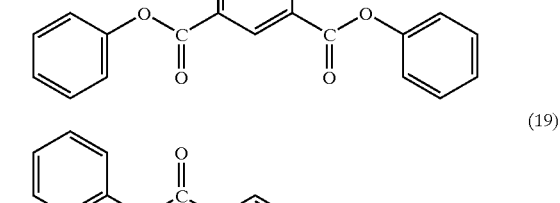
(19)
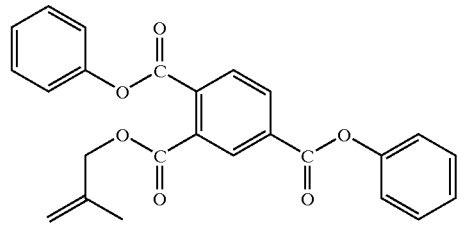
(20)
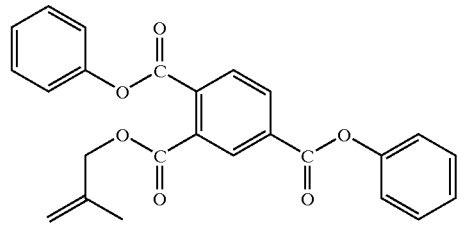
(21)
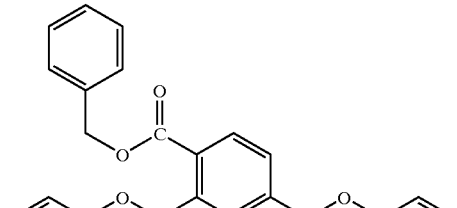
(22)
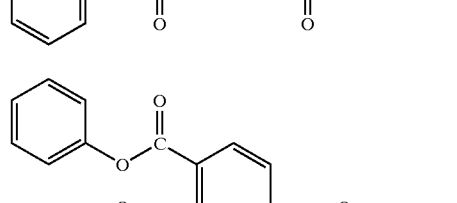
(23)
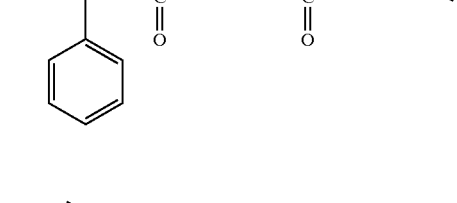
(24)
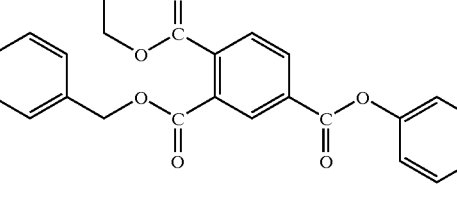
(25)
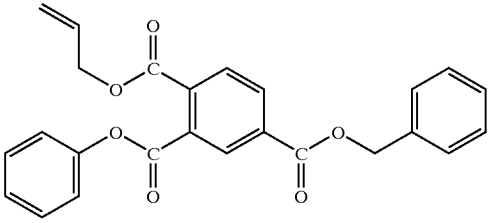

(26)
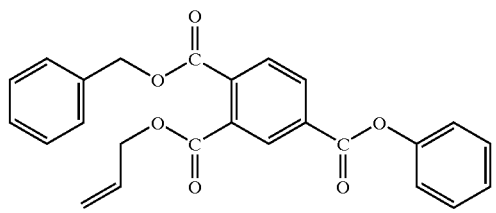

(27)
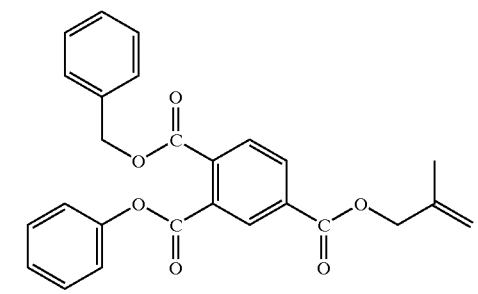

(28)
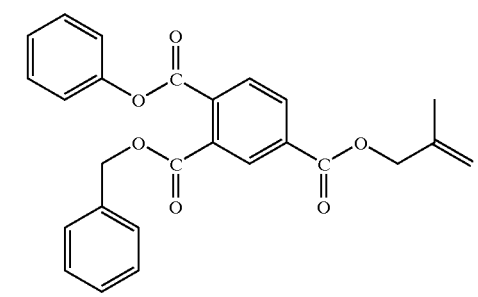

(29)
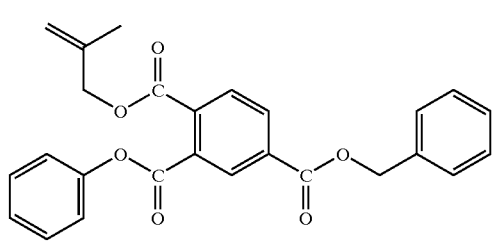

(30)
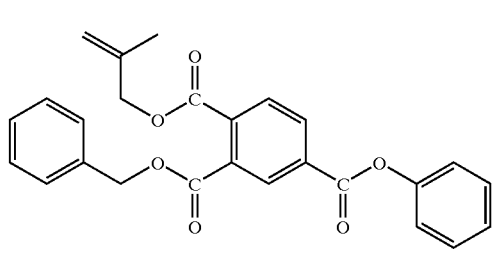

(31)
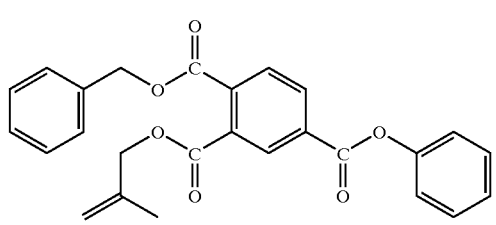

(32)
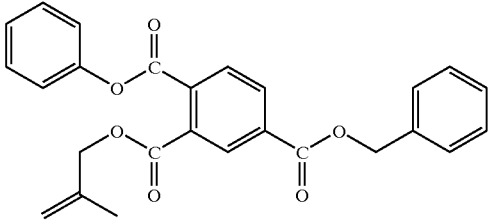

Needless to say, the present invention is not limited to these specific examples.

Among these compounds, preferred are allyl p-phenylbenzoate, methallyl p-phenylbenzoate, allyl m-phenylbenzoate, methallyl m-phenylbenzoate, allyl o-phenylbenzoate, methallyl o-phenylbenzoate, diphenyl maleate, dibenzyl maleate, diphenyl fumarate, dibenzyl fumarate, vinyl benzoate, allyl α-naphthoate, methallyl α-naphthoate, allyl β-naphthoate, methallyl β-naphthoate and compounds represented by Structural Formulae (3) to (32), and taking into account the easy availability of starting materials, most preferred are allyl p-phenylbenzoate, diphenyl maleate, dibenzyl maleate, diphenyl fumarate, dibenzyl fumarate, vinyl benzoate, allyl α-naphthoate, allyl β-naphthoate and compounds represented by structural formulae (3), (5), (7), (9), (11), (13), (15), (17), (19) and (21) to (26).

In the present invention, the amount of Component C blended varies depending on other compounds used. In the case where the compound of the present invention (I) and the polyfunctional compound used are both bifunctional compounds, Component (C) is preferably used in a range not exceeding 20% by mass, based on whole curable components.

In the case where a trifunctional compound or a compound having a greater functional group within one molecule is contained, Component (C) can be added in an amount of 20% by mass or more. In general, the amount of Component (C) blended based on whole curable components can be expressed by the following formula:

$$0 \leq \% \text{ by mass of Component (C) blended based on whole curable components}$$

$$\leq 20 + \sum_{n=2}^{\infty} ((n-2) \times \binom{\% \text{ by mass of } n\text{-functional compound}}{\text{based on whole curable components}})$$

wherein n is an integer of 2 or more.

The above formula shows that when whole curable components consist only of a bifunctional compound and Component (C), the right hand side of the above formula is $20+(2-2)_x(\%$ by mass of bifunctional compound based on whole curable components)=20.

On the other hand, when whole curable components are consist of a trifunctional compound, a bifunctional compound and Component (C), the right hand side is $20+(2-2) \times (\%$ by mass of compound based on whole curable components$)+(3-2)_x(\%$ by mass of trifunctional compound based on whole curable components$)=20+(\%$ by mass of trifunctional compound based on whole curable components).

If the amount blended of Component (C) based on whole curable components in the composition of the present invention exceeds the right hand side of the above formula, the heat resistance of the cured product disadvantageously decreases.

The present invention (IV) is a plastic lens composition comprising from 0.1 to 10 parts by mass of at least one radical polymerization initiator per 100 parts by mass of whole curable components in the plastic lens composition of the present invention (III).

In the plastic lens composition of the present invention (IV), a radical polymerization initiator can be, and is preferably, added as a curing agent.

The radical polymerization initiator which can be added to the plastic lens composition of the present invention (IV) is not particularly limited and a known radical polymerization initiator may be used insofar as it does not adversely affect the physical values such as optical properties of the plastic lens obtained by curing the composition.

The radical polymerization initiator for use in the present invention is, however, preferably soluble in other components present in the composition to be cured and at the same time, generates free radicals at 30 to 120° C. Specific examples of the radical polymerization initiator which can be added include diisopropylperoxy dicarbonate, dicyclohexylperoxy dicarbonate, di-n-propylperoxy dicarbonate, di-sec-butylperoxy dicarbonate and tert-butyl perbenzoate, but the present invention is not limited thereto. In view of curability, radical polymerization initiators having a structure represented by the following formula (33) are preferred.

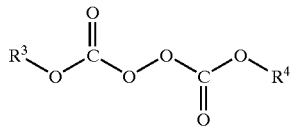

(33)

wherein $R^3$ and $R^4$ each independently represents a group selected from the group consisting of an alkyl group having from 1 to 10 carbon atoms, a substituted alkyl group, a phenyl group and a substituted phenyl group.

Specific examples of the radical polymerization initiator represented by formula (33) include di-n-propylperoxy dicarbonate, diisopropylperoxy dicarbonate, bis(4-tert-butylcyclohexyl)peroxy dicarbonate, di-2-ethoxyethylperoxy dicarbonate, di-2-ethylhexylperoxy bicarbonate, di-3-methoxybutylperoxy dicarbonate, di-sec-butylperoxy dicarbonate and di(3-methyl-3-methoxybutyl) peroxy dicarbonate. Among these, preferred are di-n-propylperoxy dicarbonate, diisopropylperoxy bicarbonate, di-2-ethoxyethylperoxy dicarbonate, di-2-ethylhexylperoxy dicarbonate and di(3-methyl-3-methoxybutyl)peroxy bicarbonate, and more preferred is diisopropylperoxy dicarbonate.

The amount of the radical polymerization initiator added is from 0.1 to 10 parts by mass, preferably from 1 to 5 parts by mass, per 100 parts by mass of whole curable components in the plastic lens composition of the present invention (III). If the amount added is less than 0.1 parts by mass, insufficient curing of the composition may result. Also, addition in excess of 10 parts by mass is not preferred in view of profitability.

Considering the cast working property, the plastic lens composition of the present invention (III) or (IV) generally has a viscosity of 500 mPa·s or less, preferably 400 mPa·s or less, still more preferably 300 mPa·s or less, at 25° C.

The term "viscosity" as used herein is a value measured by a rotational viscometer and the details of the rotational viscometer are described in Iwanami Rikagaku Jiten, Dai 3-Pan (Iwanami Encyclopedia of Physics and Chemistry, 3rd Ed.), 3rd ed., 8th imp. (Jun. 1, 1977).

The plastic lens composition of the present invention (III) or (IV) may contain additives generally used for improving the capability of plastic lenses, such as coloring agent (e.g., dye, pigment), mold-releasing agent, ultraviolet absorbent, light stabilizer and antioxidant.

Examples of the coloring agent include organic pigments such as anthraquinone type, azo type, carbonium type, quinoline type, quinoneimine type, indigoid type and phthalocyanine type; organic dyes such as azoic dye and sulfur dye; and inorganic pigments such as titanium yellow, yellow iron oxide, zinc yellow, chrome orange, molybdenum red, cobalt violet, cobalt blue, cobalt green, chromic oxide, titanium oxide, zinc sulfide and carbon black. Needless to say, the present invention is not limited to these specific examples.

Examples of the mold-releasing agent include stearic acid, butyl stearate, zinc stearate, stearic acid amide, fluorine-containing compounds and silicone compounds. Needless to say, the present invention is not limited to these specific examples.

The ultraviolet absorbent and light stabilizer are not particularly limited if the ultraviolet absorbent or stabilizer selected can be blended in the composition, but specific examples thereof include the following compounds. Needless to say, the present invention is not limited to these specific examples.

The term "ultraviolet absorbent" as used in the present specification means a material which absorbs light energy of sunlight or fluorescent light and converts it into heat energy or the like. The term "light stabilizer" as used in the present specification means a material which traps radicals generated due to photooxidation deterioration.

Specific examples of the ultraviolet absorbent include compounds having a benzotriazole structure unit described below.

Examples of the compound having a benzotriazole structure unit include the compounds represented by the following structural formulae (34) to (49).

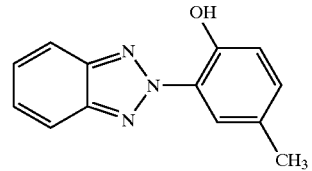

(34)

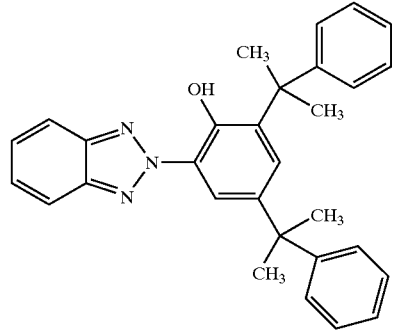

(35)

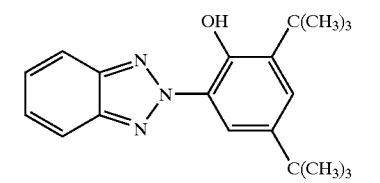 (36)
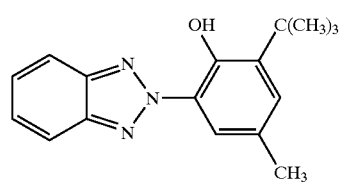 (37)
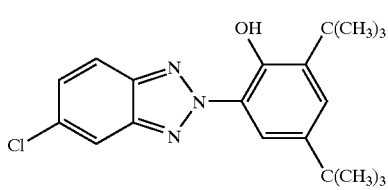 (38)
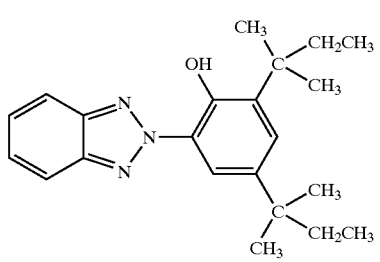 (39)
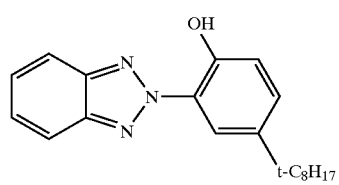 (40)
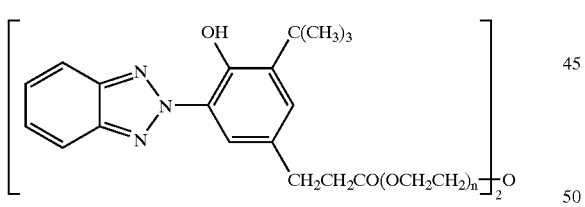 (41)
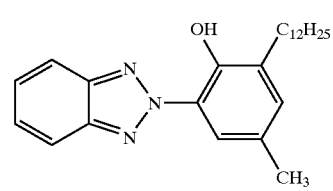 (42)
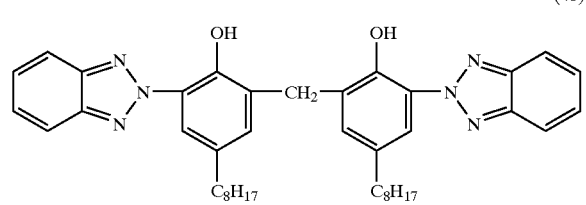 (43)
(44)
(45)
(46)
(47)
(48)
(49)
Examples of the benzophenone-based ultraviolet absorbent include the compounds of the following structural formulae (50) to (54).
(50)
(51)

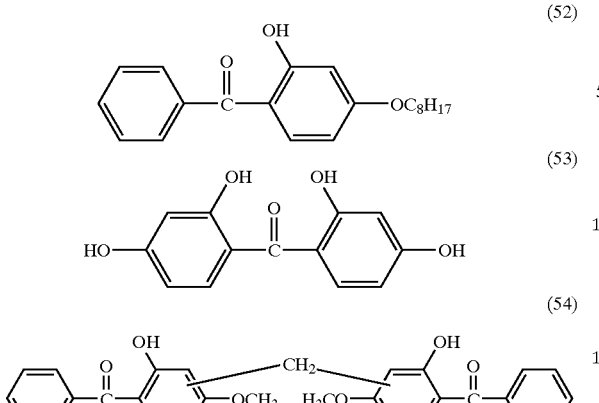

In addition, triazine-based ultraviolet absorbents represented by the following structural formula (55) and oxanilide-based ultraviolet absorbents represented by the following structural formula (56) may also be used.

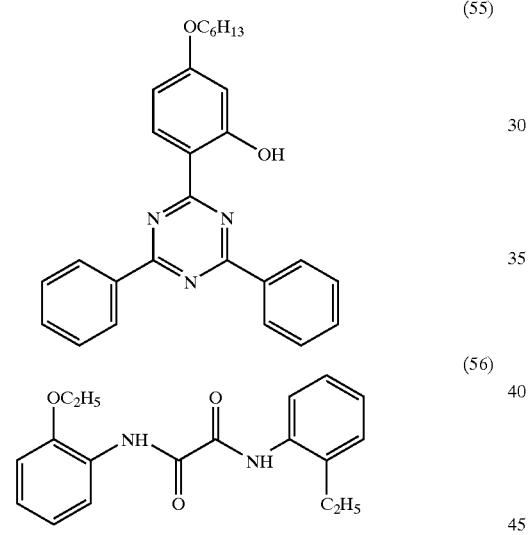

Specific examples of the light stabilizer include hindered amine-based photostabilizers (hereinafter simply referred to as "HALS") represented by the following structural formulae (57) to (64), (66) and (68) to (71):

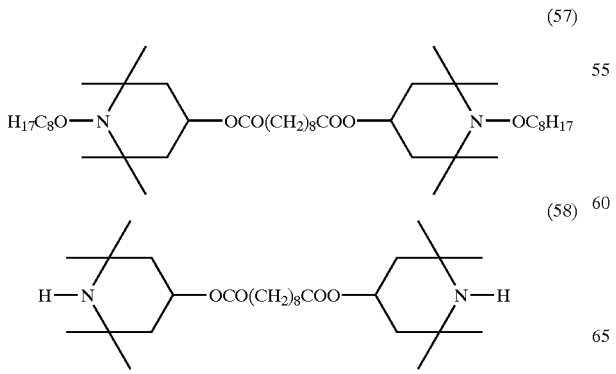

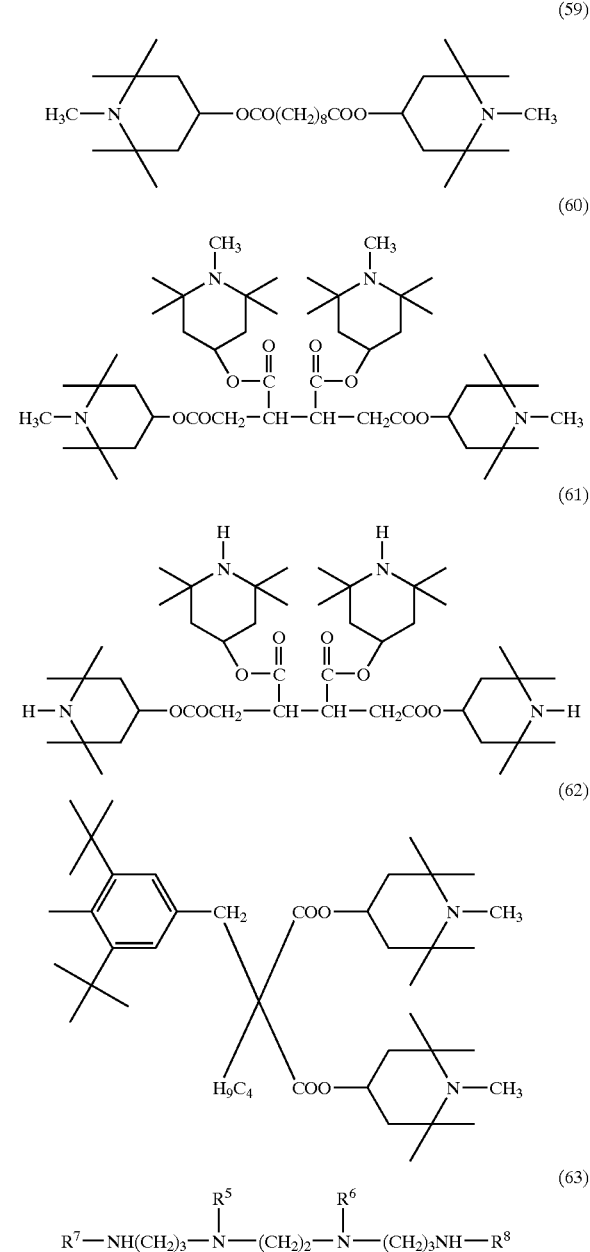

wherein $R^5$, $R^6$, $R^7$ and $R^8$ each represents —H or

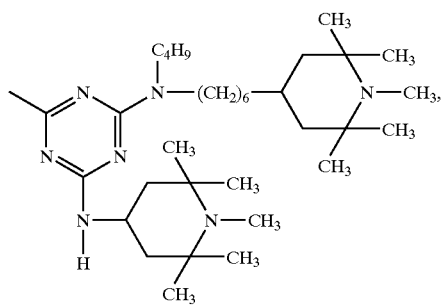

provided that the case where $R^5$, $R^6$, $R^7$ and $R^7$ are all hydrogen atoms is excluded.

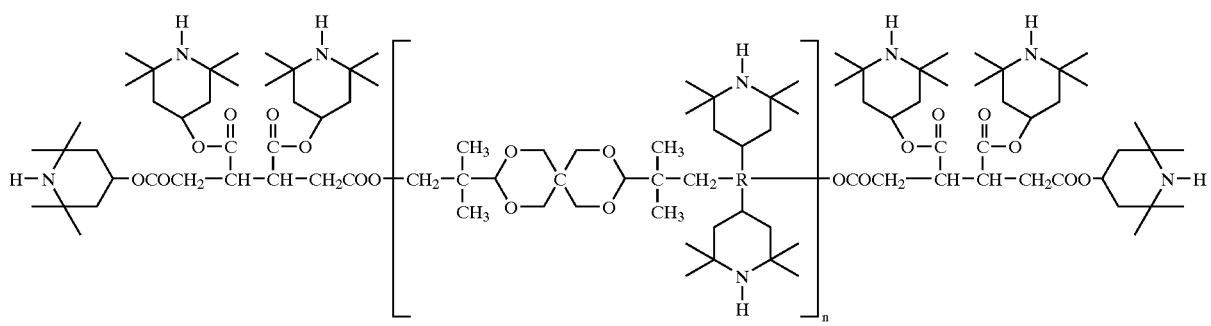
(64)

wherein R is an organic residue represented by the following structural formula (65):

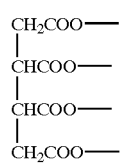
(65)

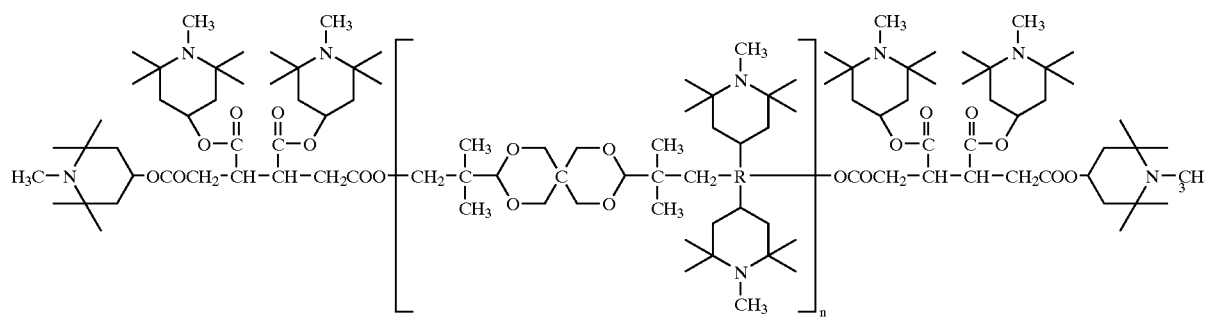
(66)

wherein R is an organic residue represented by the following structural formula (67):

(67)

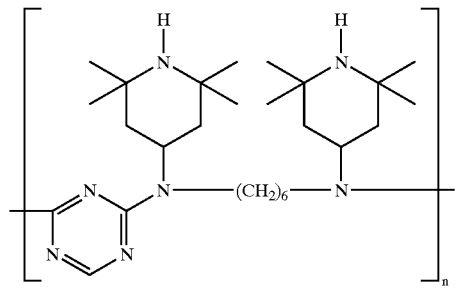

(68)

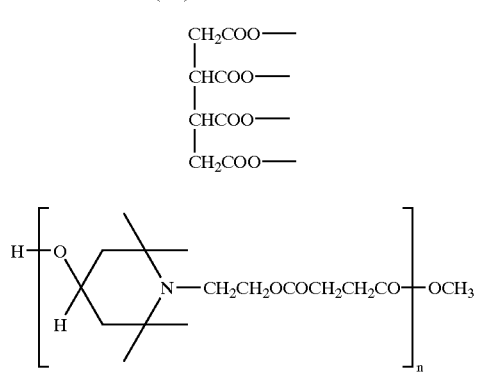

(69)

-continued

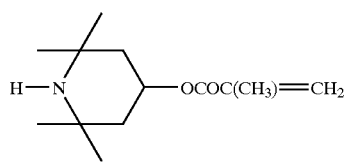
(70)

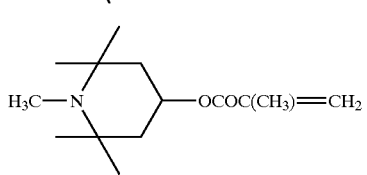
(71)

The ultraviolet absorbent and the light stabilizer may be used in combination. The amount of the ultraviolet absorbent or photostabilizer used is preferably from 0.001 to 2% by mass, more preferably from 0.05 to 1.5% by mass, based on whole curable components. If the amount added is less than 0.05% by mass, the effect of preventing deterioration cannot be fully brought out and also, use in excess of 2% by mass is not preferred in view of coloration at curing or profitability.

Examples of the antioxidant which can be used include general antioxidants such as a phenol-based antioxidant, a phosphite-based antioxidant and a thioether-based antioxidant.

Specific examples of the phenol-based antioxidant include the following compounds.

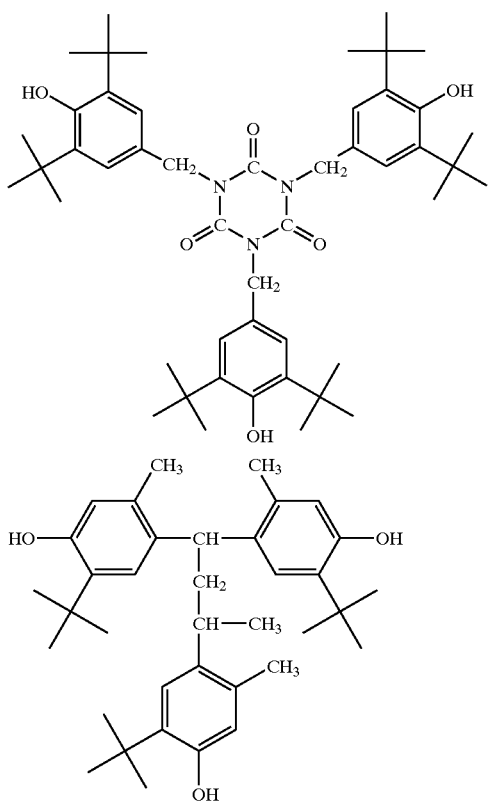
(72)
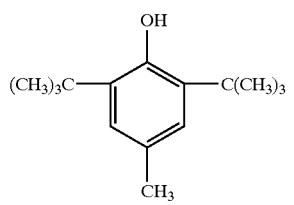
(73)
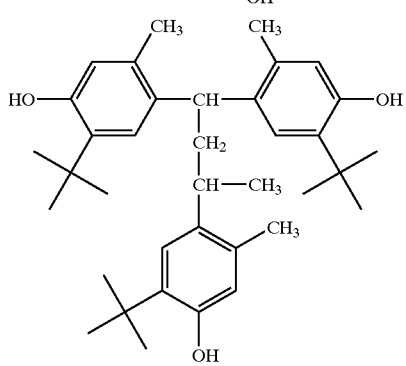
(74)
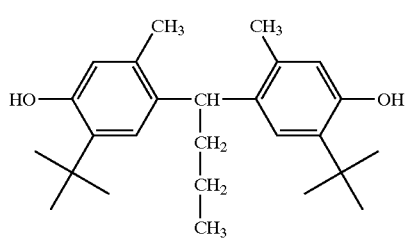
(75)
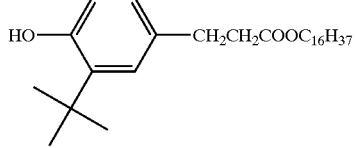
(76)
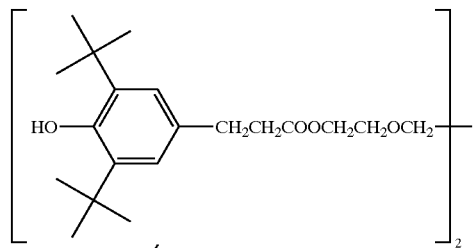
(77)
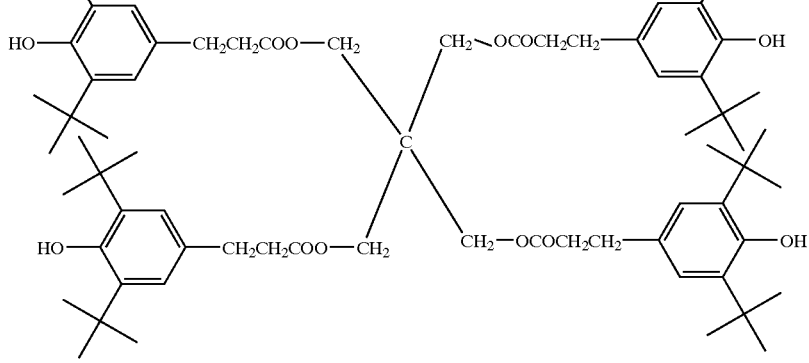
(78)
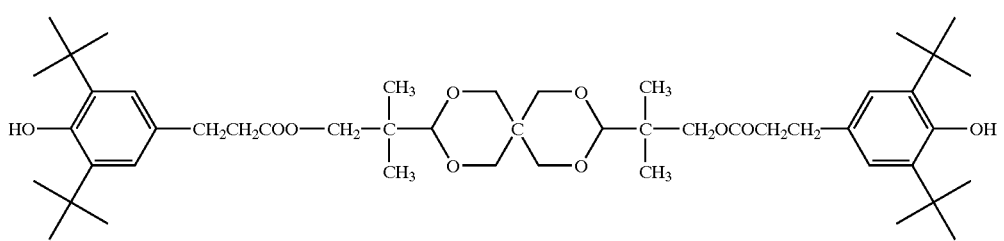
(79)

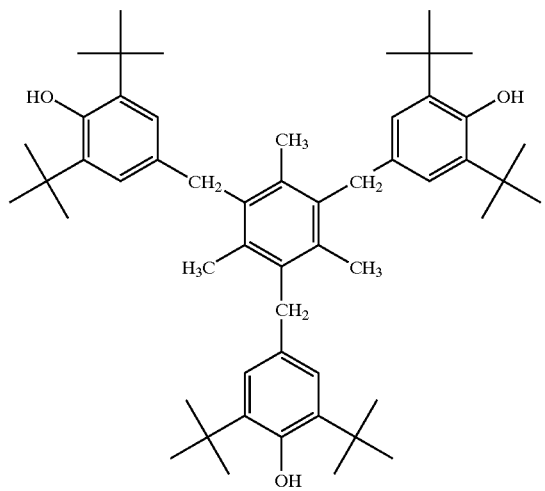
(80)
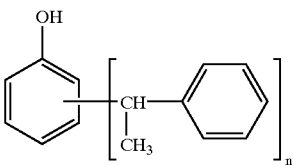
(81)
Specific examples of the phosphite-based antioxidant include the following compounds.
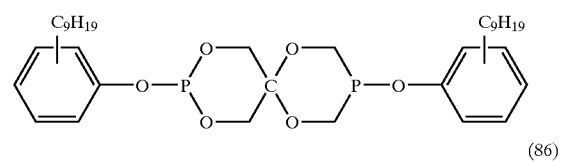
(82)
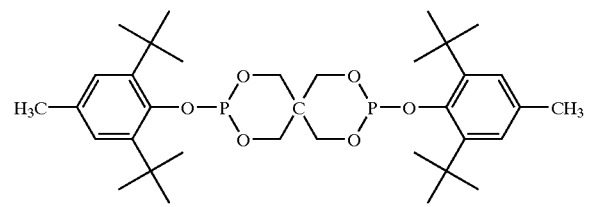
(83)
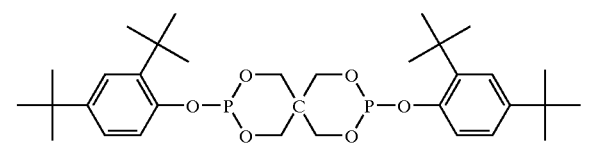
(84)
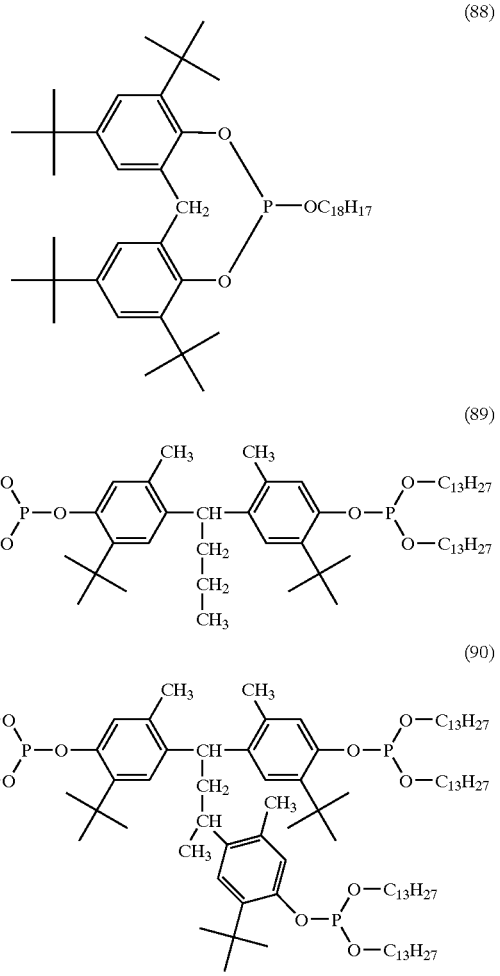
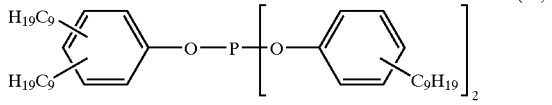
(91)

-continued

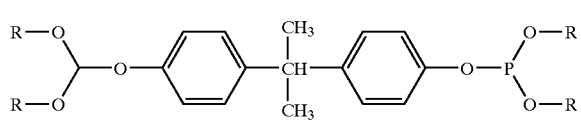
(92)

wherein R is a $C_{12}$ to $C_{15}$ alkyl group.

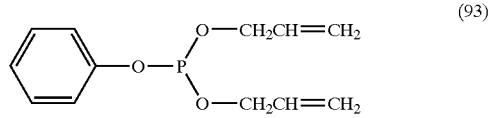
(93)

Specific examples of the thioether-based antioxidant include the following compounds.

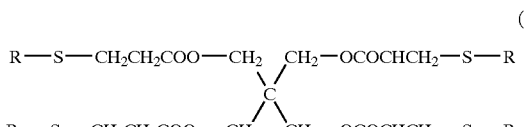
(94)

wherein R is a $C_{12}$ to $C_{15}$ alkyl group.

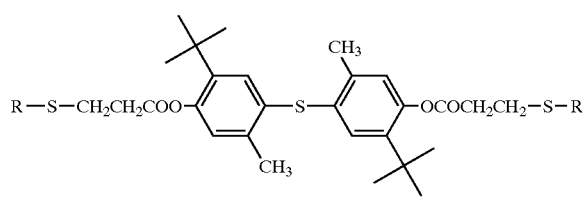
(95)

wherein R is a $C_{12}$ to $C_{15}$ alkyl group.

$H_{25}C_{12}$—OCOCH$_2$CH$_2$—S—CH$_2$CH$_2$COO—$C_{12}H_{25}$ (96)

$H_{27}C_{13}$—OCOCH$_2$CH$_2$—S—CH$_2$CH$_2$COO—$C_{13}H_{27}$ (97)

$H_{29}C_{14}$—OCOCH$_2$CH$_2$—S—CH$_2$CH$_2$COO—$C_{14}H_{29}$ (98)

$H_{37}C_{18}$—OCOCH$_2$CH$_2$—S—CH$_2$CH$_2$COO—$C_{16}H_{37}$ (99)

This antioxidant can be used in combination with the ultraviolet absorbent or light stabilizer.

The amount of the antioxidant used is preferably from 0.01 to 5% by mass, more preferably from 0.1 to 3% by mass, based on whole curable components. If the amount added is less than 0.01% by mass, the effect of preventing deterioration cannot be fully realized, and also, use in excess of 5% by mass is disadvantageous in view of profitability.

In the plastic lens composition of the present invention, a fluorescent brightening agent or the like, such as 2,5-bis[5-tert-butylbenzoxazolyl(2)]thiophene (compound of the following structural formula (100)) may be added.

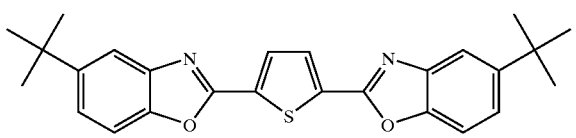
(100)

The present invention (V) and the present invention (VI) will now be described below.

The present invention (V) is a plastic lens obtained by curing the plastic lens composition described in any one of the present inventions (I) to (IV).

The present invention (VI) is a process for producing the plastic lens of the present invention (V).

In the present invention, the mold-processing of the plastic lens composition is suitably performed by a cast molding method. Specific examples of the method include a method of performing the molding by adding a radical polymerization initiator to the composition, filling the composition into a mold fixed with an elastomer gasket or spacer through a line, and heat-curing it in an oven.

The construction material used here for the mold is metal or glass. In general, the mold for plastic lenses must be cleaned after the cast-molding and such cleaning is usually performed using a strong alkali solution or a strong acid. Unlike metal, glass is virtually unchanged in terms of quality by the cleaning and can be easily polished and thereby its surface roughness greatly reduced. For these reasons, glass is preferably used.

The curing temperature at the time of molding the plastic lens composition described in either one of the present inventions (III) and (IV) is from about 30 to 120° C., preferably from 40 to 100° C. Taking into account shrinkage or strain at the time of curing, the curing temperature is preferably facilitated by way of a method which allows the curing to proceed gradually while raising the temperature. The curing time is generally from 0.5 to 100 hours, preferably from 3 to 50 hours, more preferably from 10 to 30 hours.

The plastic lens of the present invention can be dyed similarly to normal plastic lenses.

The method for dyeing the plastic lens of the present invention is not particularly limited and any method may be used insofar as it is a dyeing method for known plastic lenses. Among these, a dip dyeing method conventionally known as a general method is preferred. The term "dip dyeing method" as used herein means a method of dispersing a disperse dye together with a surfactant in water to prepare a dyeing solution and dipping a plastic lens in this dyeing solution under heating, thereby dyeing the plastic lens.

The method for dyeing the plastic lens is not limited to this dip dyeing method but other known methods may be used, for example, a method of sublimating an organic pigment and thereby dyeing a plastic lens (see, JP-B-35-1384 (the term "JP-B" as used herein means "Japanese examined patent publication")) or a method of sublimating a sublimable dye and thereby dyeing a plastic lens (see, JP-B-56-159376 and JP-B-1-277814) may be used. n view of easiness and simplicity of operation, the dip dyeing method is most preferred.

The present invention is further illustrated below with reference to examples. However, the present invention should not be construed as being limited thereto.

Various physical properties were measured as follows.

1. Refractive Index ($n_D$) and Abbe Number ($v_D$)

A test piece of 9 mm×16 mm×4 mm was prepared and measured in terms of refractive index ($n_D$) and Abbe number ($v_D$) at room temperature using "Abbe Refractometer manufactured by Atago. The contact solvent used was α-bromonaphthalene.

2. Viscosity

The viscosity was measured at 25° C. using a B-Type viscometer (Model BIU) manufactured by Tokyo Keiki Co., Ltd.

3. Barcol Hardness

The Barcol hardness was measured using Model 934-1 according to JIS K 6911.

4. Specific Gravity of Cured Material

The specific gravity of the cured material after curing was measured by the sink-float method (at 23° C.) of JIS K 7112.

PRODUCTION EXAMPLE 1

Production of Sample A

Figure 2:
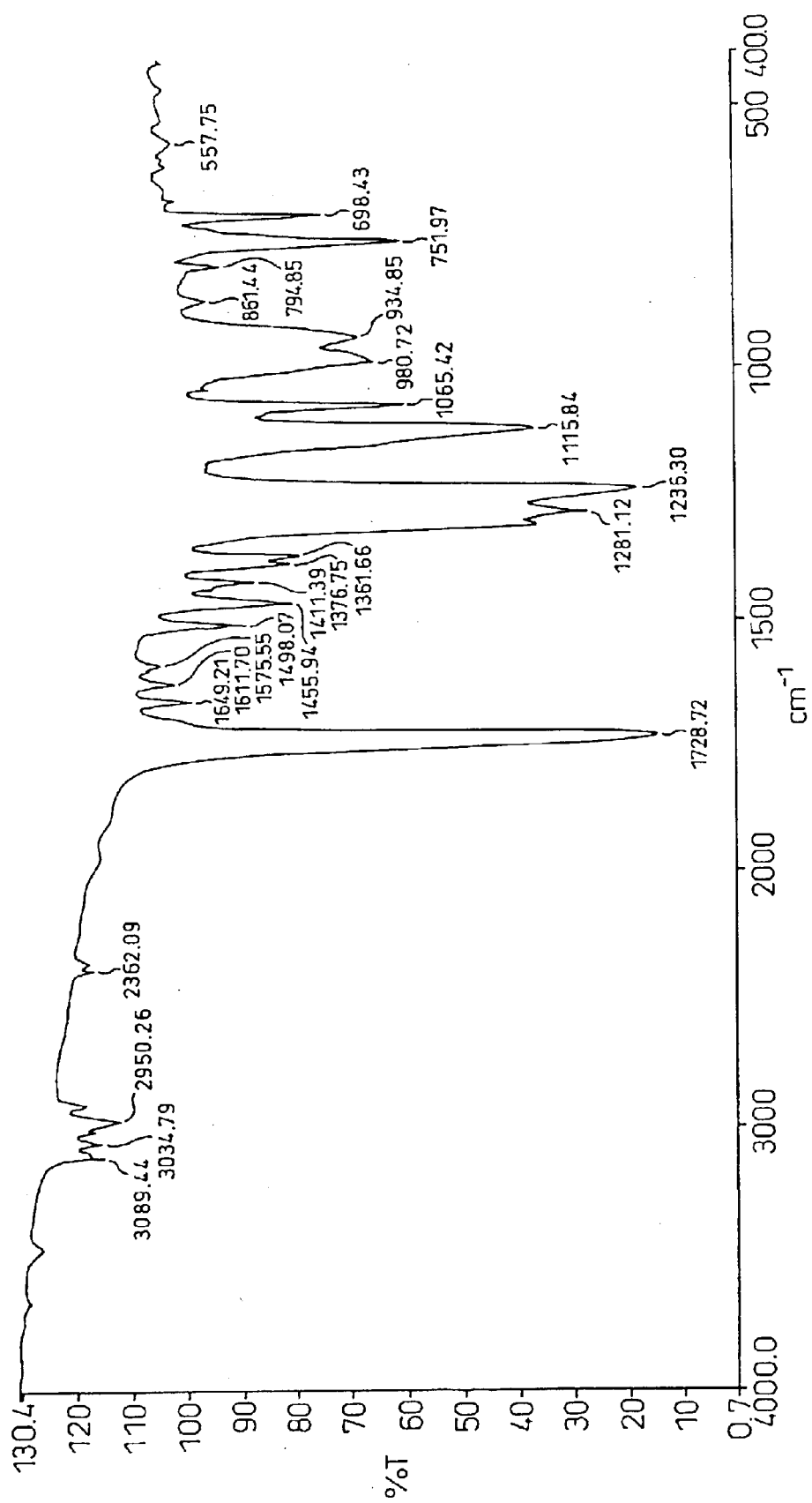
FIG. 2 is a FT-IR spectrum chart of the allyl ester compound produced in Production Example 1.

Into a 1 L three-neck flask with a distillation unit, 660.7 g (2.0 mol) of triallyl 1,2,4-benzenetricarboxylate, 216.3 g (2.0 mol) of benzyl alcohol and 0.661 g (0.1% by mass (based on triallyl 1,2,4-benzenetricarboxylate)) of dibutyltin oxide were charged. The system was heated at 180° C. in a nitrogen stream to distill off allyl alcohol generated. When about 81 g of allyl alcohol was distilled off, the pressure inside the reaction system was reduced to 1.33 kPa to raise the distillation rate of allyl alcohol. After a theoretical amount (116.2 g) of allyl alcohol was distilled off, the system was further heated for one hour and then kept at 180° C. and 0.13 KPa for one hour. Thereafter, the reactor was cooled to obtain 760.1 g of an allyl ester compound (hereinafter referred to as "Sample A"). FIG. 1 and FIG. 2 show 400 MHz $^1$H-NMR spectrum (solvent: CDCl$_3$) and FT-IR spectrum of Sample A obtained, respectively.

As a result of analysis by high-performance liquid chromatography (column used: Shodex C8-5B manufactured by Showa Denko K.K., column temperature: 40° C., elution solvent: water:acetonitrile (7:3 (vol/vol)) mixed solution, flow rate: 1 ml/min, detector: UV detector), Sample A was found to contain 25% by mass of triallyl 1,2,4-benzenetricarboxylate, 4% by mass of tribenzyl 1,2,4-benzenetricarboxylate, 45% by mass of the compound represented by the following formula (101) and 26% by mass of the compound represented by the following formula (102).

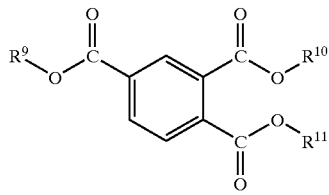
(101)

wherein $R^9$, $R^{10}$ and $R^{11}$ each represents an allyl group or a benzyl group, provided that one of $R^9$, $R^{10}$ and $R^{11}$ is a benzyl group and two others are an allyl group.

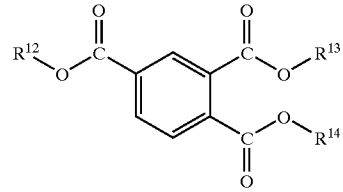
(102)

wherein $R^{12}$, $R^{13}$ and $R^{14}$ each represents an allyl group or a benzyl group, provided that one of $R^{12}$, $R^{13}$ and $R^{14}$ is an allyl group and two others are a benzyl group.

PRODUCTION EXAMPLE 2

Production of Sample B

Figure 3:
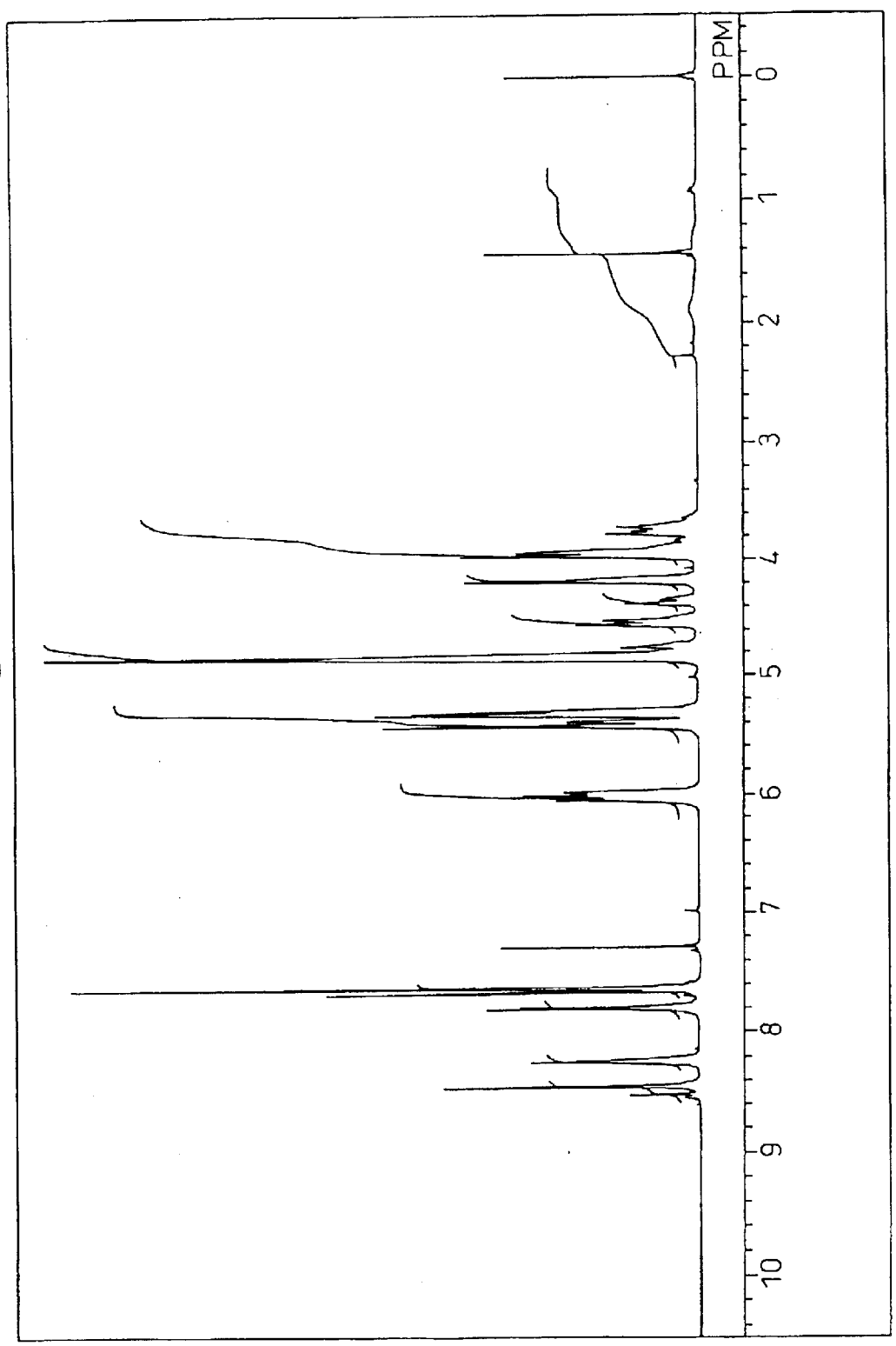
FIG. 3 is a 400 MHz $^1$H-NMR spectrum chart of the allyl ester compound produced in Production Example 2.
Figure 4:
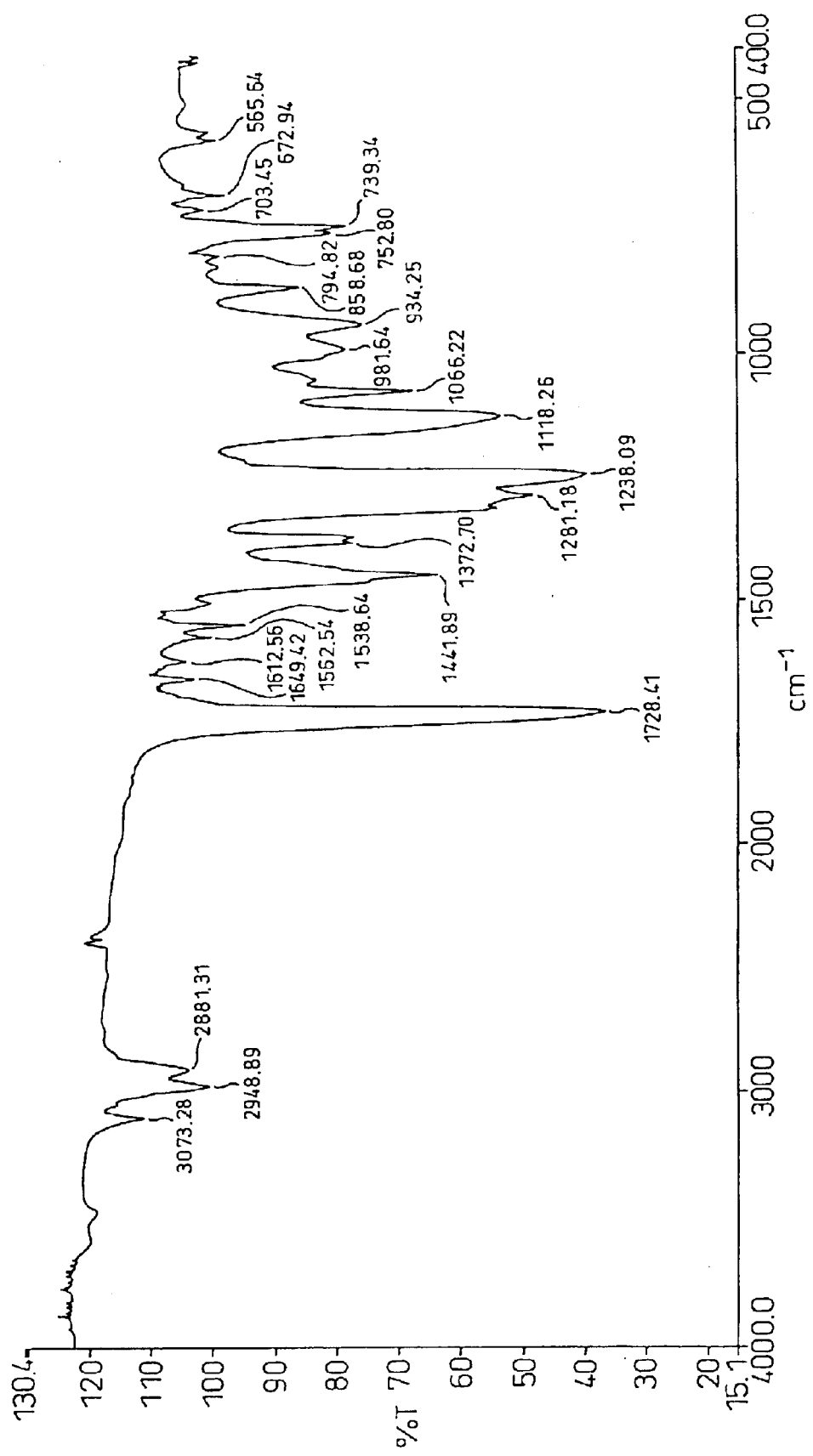
FIG. 4 is a FT-IR spectrum chart of the allyl ester compound produced in Production Example 2.

Into a 3 L three-neck flask with a distillation unit, 330.3 g (1.0 mol) of triallyl 1,2,4-benzenetricarboxylate, 418.9 g (1.0 mol) of ethylene oxide 2 mol adduct of 2,4,6-tribromophenol and 0.33 g (0.1% by mass (based on triallyl 1,2,4-benzenetricarboxylate)) of dibutyltin oxide were charged. The system was heated at 180° C. in a nitrogen stream to distill off allyl alcohol generated. When about 45 g of allyl alcohol was distilled off, the pressure inside the reaction system was reduced to 1.33 kPa to raise the distillation rate of allyl alcohol. After a theoretical amount (58.1 g) of allyl alcohol was distilled off, the system was further heated for one hour and then kept at 180° C. and 0.13 KPa for one hour. Thereafter, the reactor was cooled to obtain 691.2 g of an allyl ester compound (hereinafter referred to as "Sample B"). FIG. 3 and FIG. 4 show the 400 MHz $^1$H-NMR spectrum (solvent: CDCl$_3$) and the FT-IR spectrum of Sample B obtained, respectively.

As a result of analysis by high-performance liquid chromatography (column used: Shodex C8-5B manufactured by Showa Denko K.K., column temperature: 40° C., elution solvent: water:acetonitrile (7:3 (vol/vol)) mixed solution, flow rate: 1 ml/min, detector: UV detector), Sample B was found to contain 15% by mass of triallyl 1,2,4-benzenetricarboxylate, 6% by mass of the compound represented by the following structural formula (103), 45% by mass of the compound represented by the following formula (104) and 34% by mass of the compound represented by the following formula (10.5).

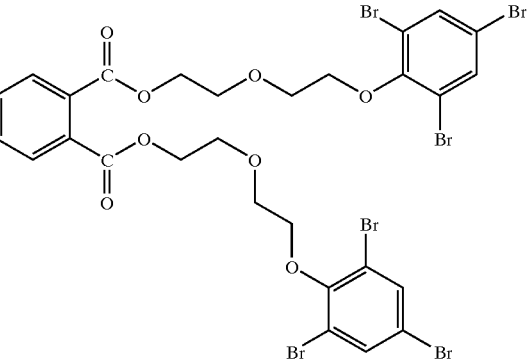
(103)

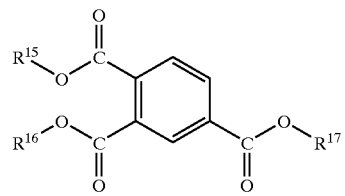
(104)

wherein $R^{15}$, $R^{16}$ and $R^{17}$ each represents an allyl group or a 2,4,6-tribromophenoxyethoxyethyl group, provided that one of $R^{15}$, $R^{16}$ and $R^{17}$ is a 2,4,6-tribromophenoxyethoxyethyl group and two others are an allyl group.

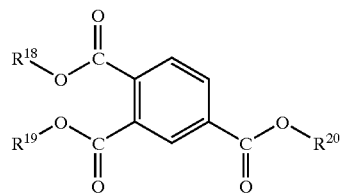

(105)

wherein $R^{18}$, $R^{19}$ and $R^{20}$ each represents an allyl group or a 2,4,6-tribromophenoxyethoxyethyl group, provided that one of $R^{18}$, $R^{19}$ and $R^{20}$ is an allyl group and two others are a 2,4,6-tribromophenoxyethoxyethyl group.

PRODUCTION EXAMPLE 3

Production of Sample C

Into a 2 L three-neck round bottom flask equipped with a reflux condenser with Dean-Stark trap, 250 g (1.3 mol) of 1,2,4-benzenetricarboxylic anhydride, 75.6 g (1.3 mol) of allyl alcohol, 400 g of toluene and 5 g of p-toluenesulfonic acid (2% by mass (based on 1,2,4-benzenetricarboxylic anhydride)) were charged. After adjusting the temperature of an oil bath to 120° C., the reaction was initiated. During the reaction, the purified water was removed from the 3 L three-neck round bottom flask using the Dean-Stark trap. After 5 hours, a small amount of the reaction solution was sampled and the residual amount of allyl alcohol was confirmed by gas chromatography. As a result, the residual amount was found to be about 1% of the amount charged. Then, 140.7 g (1.3 mol) of benzyl alcohol was added to the 2 L three-neck round bottom flask and the reaction further continued for 15 hours. Thereafter, a small amount of the reaction solution was sampled and the residual amount of benzyl alcohol was confirmed by gas chromatography. As a result, the residual amount was found to be about 1% of the amount charged.

Figure 5:
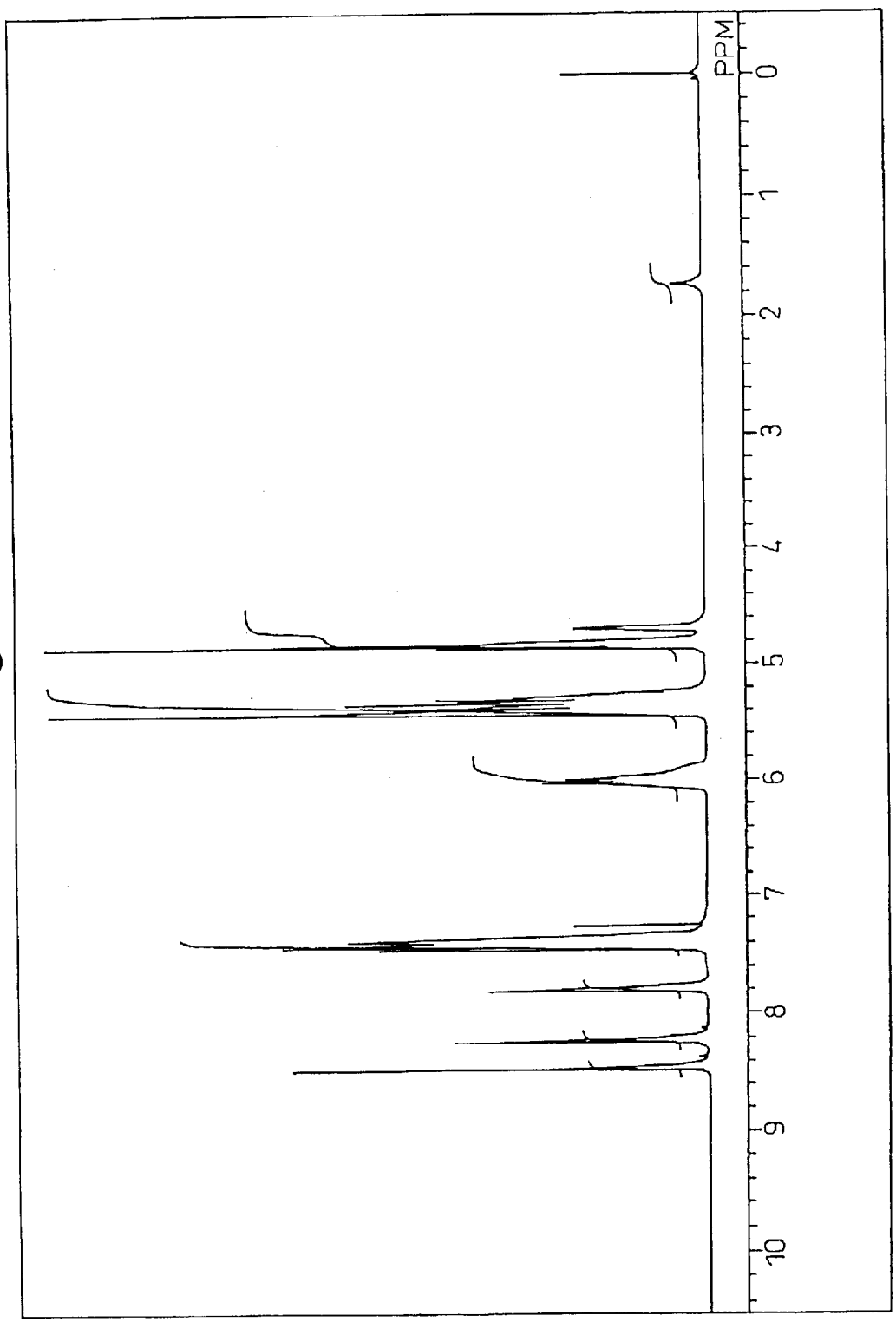
FIG. 5 is a 400 MHz $^1$H-NMR spectrum chart of the allyl ester compound produced in Production Example 3.
Figure 6:
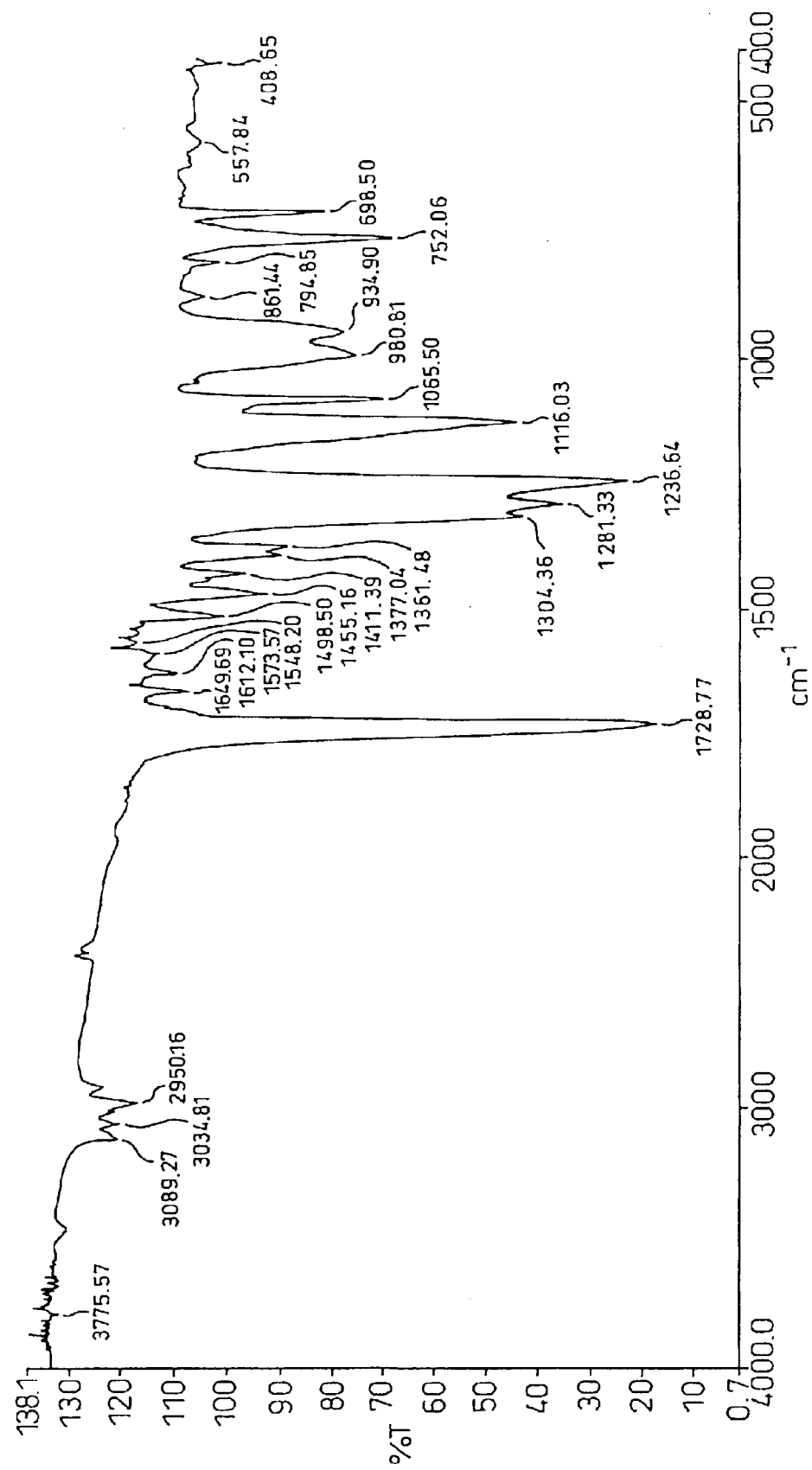
FIG. 6 is a FT-IR spectrum chart of the allyl ester compound produced in Production Example 3.

Subsequently, 113.4 g (1.95 mol) of allyl alcohol was added to the 2 L three-neck round bottom flask and the reaction further continued for 15 hours. Thereafter, the reaction was terminated and the solution in the three-neck round bottom flask was transferred to a 5 L -separating funnel. Into this 5 L separating funnel, 500 g of an aqueous 1% by mass sodium hydroxide solution was charged, the separating funnel was shaken and then left standing, and the aqueous phase was removed. Furthermore, 500 g of an aqueous 1% by mass sodium hydroxide solution was charged into the 5 L separating funnel and the same operation as above was performed. Thereafter, 500 g of pure water was charged twice into the 5 L separating funnel and the same operation was repeated twice. After this, toluene and excess allyl alcohol was removed from the organic phase by distillation using an evaporator to obtain 490.5 g of a liquid (hereinafter referred to as "Sample C"). FIG. 5 and FIG. 6 show the 400 MHz $^1$H-NMR spectrum (solvent: CDCl$_3$) and the FT-IR spectrum of Sample C obtained, respectively.

As a result of analysis by high-performance liquid chromatography (column used: Shodex C8-5B manufactured by Showa Denko K.K., column temperature: 40° C., elution solvent: water:acetonitrile (7:3 (vol/vol)) mixed solution, flow rate: ml/min, detector: UV detector), Sample C was found to contain 26% by mass of triallyl 1,2,4-benzenetricarboxylate, 4% by mass of tribenzyl 12,4-benzenetricarboxylate, 45% by mass of the compound represented by formula (101) and 25% by mass of the compound represented by formula (102).

PRODUCTION EXAMPLE 4

Production of Sample D

Into a 1 L three-neck flask with a distillation unit, 660.7 g (2.0 mol) of triallyl 1,3,5-benzenetricarboxylate, 216.3 g (2.0 mol) of benzyl alcohol and 0.661 g (0.1% by mass (based on triallyl 1,3,5-benzenetricarboxylate)) of dibutyltin oxide were charged. The system was heated at 180° C. in a nitrogen stream to distill off allyl alcohol generated. When about 81 g of allyl alcohol was distilled off, the pressure inside the reaction system was reduced to 1.33 kPa to raise the distillation rate of allyl alcohol. After a theoretical amount (116.2 g) of allyl alcohol was distilled off, the system was further heated for one hour and then kept at 180° C. and 0.13 KPa for one hour. Thereafter, the reactor was cooled to obtain 760.1 g of an allyl ester compound (hereinafter referred to as "Sample D").

As a result of analysis by high-performance liquid chromatography (column used: Shodex C8-5B manufactured by Showa Denko K.K., column temperature: 40° C., elution solvent: water:acetonitrile (7:3 (vol/vol)) mixed solution, flow rate: 1 ml/min, detector: UV detector), Sample D was found to contain 25% by mass of triallyl 1,3,5-tricarboxylate, 4% by mass of tribenzyl 1,3,5-tricarboxylate, 45% by mass of benzyldiallyl 1,3,5-tricarboxylate and 26% by mass of allyldibenzyl 1,3,5-tricarboxylate.

PRODUCTION EXAMPLE 5

Production of Compound

Represented by Structural Formula (106) Into a 3 L three-neck flask with a distillation unit, 1,470 g (5.97 mol) of diallyl terephthalate, 158.2 g (0.5 mol) of 2 mol ethylene oxide adduct of bisphenol A and 1.47 g (0.1% by mass (based on diallyl terephthalate)) of dibutyltin oxide were charged. The system was heated at 180° C. in a nitrogen stream to distill off allyl alcohol generated. When about 45 g of allyl alcohol was distilled off, the pressure inside the reaction system was reduced to 1.33 kPa to raise the distillation rate of allyl alcohol. After a theoretical amount (58.1 g) of allyl alcohol was distilled off, the system was further heated for one hour and then kept at 190° C. and 0.13 kPa for one hour. Thereafter, the reactor was cooled to obtain 1,570.1 g of a product containing an allyl ester compound represented by structural formula (106).

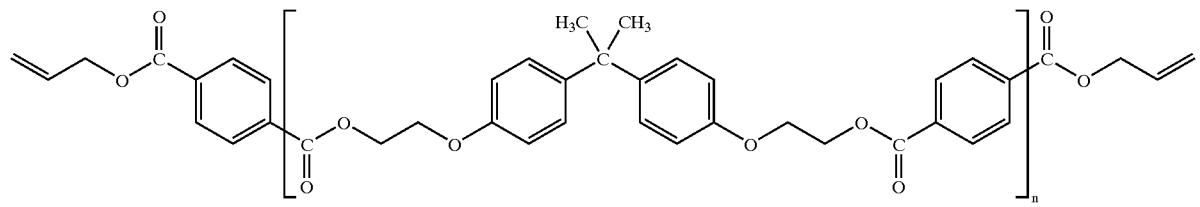

(106)

wherein n is an integer of 1 or more.

As a result of analysis by gas chromatography (GC-14B manufactured by Shimadzu Corporation, hydrogen flame ionization detector, column used: OV-17 of 0.5 m, column temperature: constant at 130° C. for 4 minutes, then raised to 160° C. at 32° C./min and thereafter constant at 160° C.), the product obtained above was found to contain 75% by mass of diallyl terephthalate.

EXAMPLE 1

As shown in Table 1, 100.0 parts by mass of Sample A and 3 parts by weight of diisopropylperoxy dicarbonate (IPP) were blended and mixed with stirring to form a completely homogeneous solution composition. The viscosity at this time was measured. Thereafter, a vessel containing this solution was placed in a desiccator capable of depressurization and the pressure was reduced by means of a vacuum pump for about 15 minutes to purge gases from the solution. The resulting solution composition was injected by means of a syringe into a mold fabricated from a glass-made mold for ophthalmic plastic lenses and a resin-made gasket, while taking care to prevent intermixing of gases, and then cured in an oven according to a temperature-rising program of heating at 40° C. for 7 hours, heating at 40 to 60° C. for 10 hours, heating at from 60 to 80° C. for 3 hours, heating at 80° C. for 1 hour and heating at 85° C. for 2 hours. The lens obtained was measured in terms of refractive index, Abbe number, Barcol hardness and specific gravity. The results are shown in Table 1.

EXAMPLES 2 to 6 and COMPARATIVE EXAMPLE 1

Compositions were prepared to have a blend shown in Table 1. Thereafter, in the same manner, the viscosity was measured and after curing, the lenses were measured for refractive index, Abbe number, Barcol hardness and specific gravity. The results are shown in Table 1.

INDUSTRIAL APPLICABILITY

As is apparent from the above, according to the present invention, a novel polyvalent carboxylic acid allyl ester, a plastic lens composition using the carboxylic acid ester and a plastic lens obtained by curing the composition are provided, which can have a low viscosity, provide a cured product having a high refractive index, are free of atoms such as halogen atoms and sulfur atoms and therefore suitable for applications to optical materials, including plastic lens material.

TABLE 1

| | | | Example 1 | Example 2 | Example 3 | Example 4 | Example 5 | Example 6 | Comparative Example 1 |
|---|---|---|---|---|---|---|---|---|---|
| Blend (parts by mass) | Sample A | Triallyl 1,2,4-benzenetricarboxylate | 25 | 23 | | | | | |
| | | Compound of Formula (4) | 45 | 41.4 | | | | | |
| | | Compound of Formula (5) | 26 | 23.9 | | | | | |
| | | Tribenzyl 1,2,4-benzenetricarboxylate | 4 | 3.7 | | | | | |
| | Sample B | Triallyl 1,2,4-benzenetricarboxylate | | | 7.5 | | | 7.5 | |
| | | Compound of Formula (6) | | | 22.5 | | | 22.5 | |
| | | Compound of Formula (7) | | | 17 | | | 17 | |
| | | Compound of Structural Formula (98) | | | 3 | | | 3 | |
| | Sample C | Triallyl 1,2,4-benzenetricarboxylate | | | | 23.9 | | | |
| | | Compound of Formula (4) | | | | 41.4 | | | |
| | | Compound of Formula (5) | | | | 23 | | | |
| | | Tribenzyl 1,2,4-benzenetricarboxylate | | | | 3.7 | | | |
| | Sample D | Triallyl 1,3,5-benzenetricarboxylate | | | | | 25 | | |
| | | Benzylallyl 1,3,5-benzenetricarboxylate | | | | | 45 | | |
| | | Allyldibenzyl 1,3,5-benzenetricarboxylate | | | | | 26 | | |
| | | Tribenzyl 1,3,5-benzenetricarboxylate | | | | | 4 | | |
| | | Compound of Structural Formula (99) | | | | | | | 25 |
| | | Diallyl terephthalate | | | 32 | | | 50 | 75 |
| | | Diallyl 2,2'-biphenyldicarboxylate | | | 10 | | | | |
| | | Allyl β-naphthoate | | | 8 | 8 | | | |
| | | Allyl p-phenylbenzoate | | 8 | | | | | |
| Viscosity (25° C.) (mPa·s) | | | 152 | 100 | 300 | 100 | 150 | 280 | 144 |
| Initiator IPP (parts by mass) | | | 3 | 3 | 3 | 3 | 3 | 3 | 3 |
| Physical Properties of Cured Product | | Refractive Index $n_u$ | 1.589 | 1.594 | 1.597 | 1.595 | 1.589 | 1.589 | 1.579 |
| | | Abbe number | 34 | 30 | 33 | 30 | 34 | 34 | 34 |
| | | Barcol hardness | 45 | 44 | 48 | 44 | 44 | 48 | 46 |
| | | Specific gravity | 1.26 | 1.28 | 1.46 | 1.29 | 1.26 | 1.46 | 1.26 |

What is claimed is:

1. A plastic lens composition comprising, as an essential component, a polyvalent carboxylic acid ester, which is a trivalent or greater valent carboxylic acid ester and which has, within one molecule, two or more organic groups represented by the following formula (I) and an organic group represented by the following formula (2):

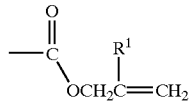
(1)

wherein each $R^1$ independently represents H or $CH_3$;

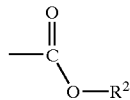
(2)

wherein $R^2$ represents an organic group derived from a compound having an aromatic ring and a hydroxyl group within one molecule; and wherein the polyvalent carboxylic acid ester is an ester of a polyvalent carboxylic acid selected from the group consisting of 1.3,5-benzenetricarboxylic acid, 1,2,4-benzenetricarboxylic acid, 1,2,3-propanetricarboxylic acid, 1,2,4,5-benzenetetracarboxylic acid and 1,2,3,4-butanetetracarboxylic acid.

2. The plastic lens composition according to claim 1, further comprising at least one radical polymerization initiator in an amount of 0.1 to 10 parts by mass per 100 parts by mass of whole curable components in the plastic lens composition.

3. The plastic lens composition according to claim 2, wherein the radical polymerization initiator is selected from the compounds represented by the following formula (33):

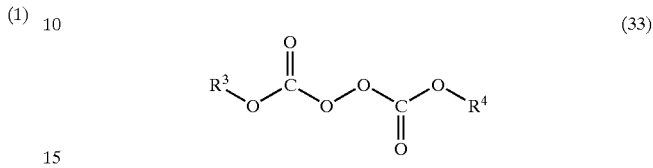
(33)

wherein $R^3$ and $R^4$ each independently represents a group selected from the group consisting of an alkyl group having from 1 to 10 carbon atoms, a substituted alkyl group, a phenyl group and a substituted phenyl group.

4. The plastic lens composition according to claim 1, which has a viscosity at 25° C. of not more than 1,000 mPa·s.

5. A plastic lens obtained by curing a plastic lens composition as set forth in claim 1.

6. A process for producing a plastic lens, comprising curing a plastic lens composition as set forth in claim 1.

7. The process according to claim 6, wherein the plastic lens composition is cured by casting polymerization at a curing temperature of 30 to 120° C. for a curing time of 0.5 to 100 hours.

* * * * *